US012678304B2

(12) United States Patent
Albertsson et al.

(10) Patent No.: US 12,678,304 B2
(45) Date of Patent: Jul. 14, 2026

(54) MECHANICAL PROSTHETIC FOOT FOR MULTIPLE ACTIVITY LEVELS

(71) Applicant: Össur Iceland ehf, Reykjavík (IS)

(72) Inventors: Aron Kristbjorn Albertsson, Reykjavík (IS); Felix Starker, Reykjavík (IS); Jeroen Nijman, Reykjavík (IS); Victoria Pamela Anne Clark, Reykjavík (IS)

(73) Assignee: ÖSSUR ICELAND EHF, Reykjavik (IS)

( * ) Notice: Subject to any disclaimer, the term of this patent is extended or adjusted under 35 U.S.C. 154(b) by 665 days.

(21) Appl. No.: 18/179,769

(22) Filed: Mar. 7, 2023

(65) Prior Publication Data

US 2023/0285168 A1      Sep. 14, 2023

Related U.S. Application Data

(60) Provisional application No. 63/269,159, filed on Mar. 10, 2022.

(51) Int. Cl.
*A61F 2/66* (2006.01)

(52) U.S. Cl.
CPC ........ *A61F 2/66* (2013.01); *A61F 2002/6671* (2013.01)

(58) Field of Classification Search
CPC ...... A61F 2002/6664; A61F 2002/6657; A61F 2002/6671; A61F 2002/6685; A61F 2/66; A61F 2/6692
See application file for complete search history.

(56) References Cited

U.S. PATENT DOCUMENTS 5,653,767 A * 8/1997 Allen ........................ A61F 2/68
                                                       623/55
6,099,572 A * 8/2000 Mosler ...................... A61F 2/66
                                                       623/53
(Continued)

FOREIGN PATENT DOCUMENTS

EP          3131505 B1 * 8/2023 ............... A61F 2/66
WO     WO-2014022411 A1 * 2/2014 ............... A61F 2/78
(Continued)

OTHER PUBLICATIONS

Invitation to Pay Additional Fees in International Application No. PCT/IB2022/051556 dated Jun. 2, 2022 in 15 pages.
(Continued)

*Primary Examiner* — Alvin J Stewart
(74) *Attorney, Agent, or Firm* — Knobbe, Martens, Olson & Bear, LLP

(57) ABSTRACT

A prosthetic foot can allow a user to engage in different activity levels, for example, walking and running using the same prosthetic foot. The prosthetic foot can have an elongate sole member, a first upper member, and a second pre-compressed upper member such that a distal end of the second upper member is biased toward the first upper member. A spacer between the distal ends of the first and second upper members can facilitate sliding of the distal end of the second upper member during ambulation to vary the stiffness of the foot. The spacer can also improve the lever arm length of the second upper member by maintaining a gap between the first and second upper members throughout ambulation.

20 Claims, 27 Drawing Sheets

(56) References Cited

U.S. PATENT DOCUMENTS

| | | | | |
|---|---|---|---|---|
| 6,241,776 B1 * | 6/2001 | Christensen | ............... | A61F 2/66 |
| | | | | 623/56 |
| 6,899,737 B1 | 5/2005 | Phillips | | |
| 9,017,421 B2 * | 4/2015 | Lecomte | ................... | A61F 2/66 |
| | | | | 623/53 |
| 9,439,786 B2 * | 9/2016 | Nijman | ..................... | A61F 2/66 |
| 2005/0187640 A1 * | 8/2005 | Christensen | .............. | A61F 2/66 |
| | | | | 623/55 |
| 2008/0183301 A1 * | 7/2008 | Christensen | .............. | A61F 2/70 |
| | | | | 623/53 |
| 2010/0023135 A1 * | 1/2010 | Rubie | ...................... | A61F 2/66 |
| | | | | 623/53 |
| 2010/0042228 A1 * | 2/2010 | Doddroe | .................. | A61F 2/76 |
| | | | | 623/53 |
| 2011/0029097 A1 * | 2/2011 | Ochoa | ...................... | A61F 2/66 |
| | | | | 623/55 |
| 2012/0179274 A1 | 7/2012 | Christensen | | |
| 2012/0271434 A1 * | 10/2012 | Friesen | ..................... | A61F 2/66 |
| | | | | 623/55 |
| 2013/0144403 A1 * | 6/2013 | Lecomte | ................... | A61F 2/66 |
| | | | | 623/53 |
| 2014/0243997 A1 * | 8/2014 | Clausen | ................... | A61F 2/70 |
| | | | | 623/55 |
| 2015/0289996 A1 * | 10/2015 | Smith | ...................... | A61F 2/66 |
| | | | | 623/53 |
| 2016/0143750 A1 | 5/2016 | Kranner et al. | | |
| 2016/0158030 A1 * | 6/2016 | Doddroe | .................. | A61F 2/66 |
| | | | | 623/50 |
| 2016/0199202 A1 * | 7/2016 | Jonasson | ................... | A61F 2/80 |
| | | | | 623/26 |
| 2016/0310298 A1 * | 10/2016 | Jonsson | ................... | A61F 2/66 |
| 2018/0263793 A1 * | 9/2018 | Clausen | ................... | A61F 2/66 |
| 2019/0015224 A1 * | 1/2019 | Smith | ....................... | A61F 2/66 |
| 2019/0125552 A1 * | 5/2019 | Day | ...................... | A61F 2/6607 |
| 2020/0179138 A1 * | 6/2020 | Anderson | ................ | A61F 2/66 |
| 2021/0259857 A1 * | 8/2021 | Phillips | .................... | A61F 2/66 |
| 2022/0031477 A1 * | 2/2022 | Anderson | ................ | A61F 2/76 |
| 2022/0168117 A1 * | 6/2022 | Clausen | ................... | A61F 2/66 |
| 2022/0273466 A1 * | 9/2022 | Nijman | ................ | A61F 2/6607 |
| 2023/0201008 A1 * | 6/2023 | Pusch | ....................... | A61F 2/68 |
| | | | | 623/53 |

FOREIGN PATENT DOCUMENTS

| | | | | |
|---|---|---|---|---|
| WO | WO-2019212593 A1 * | 11/2019 | .............. | A61F 2/66 |
| WO | WO-2021178333 A1 * | 9/2021 | .............. | A61F 2/66 |
| WO | WO 2022/180516 | 9/2022 | | |

OTHER PUBLICATIONS

International Search Report and Written Opinion in International Application No. PCT/IB2022/051556 dated Jul. 25, 2022 in 20 pages.

Invitation to Pay Additional Fees in International Application No. PCT/IB2023/052173 dated Apr. 17, 2023 in 11 pages.

Search Report and Written Opinion in corresponding International Patent Application No. PCT/IB2023/052173, dated Jun. 7, 2023, in 18 pages.

* cited by examiner

16

16

16

16

MECHANICAL PROSTHETIC FOOT FOR MULTIPLE ACTIVITY LEVELS

INCORPORATION BY REFERENCE TO ANY PRIORITY APPLICATIONS

This application claims priority to U.S. Provisional Application No. 63/269,159, filed Mar. 10, 2022, which is incorporated herein by reference. Any and all applications for which a foreign or domestic priority claim is identified in the Application Data Sheet as filed with the present application are hereby incorporated by reference under 37 CFR 1.57.

BACKGROUND

Field

The present application relates to foot prostheses in general, and more particularly, to mechanical prosthetic feet configured to allow a user to engage in multiple activity levels.

Description of the Related Art

Various types of mechanical (non-powered or passive) prosthetic foot are available as substitutes for human feet and are designed to try to replicate and/or approximate the natural function of human feet. These prosthetic feet may include various components, such as foot plates and ankle modules. Some of the foot plates can have an overall shape that mimics the shape of a natural foot, with a toe region terminating at a toe end, a heel region terminating at a heel end, and a metatarsal region and an arch region between the toe region and the heel region. Some of the foot plates can curve upwardly and rearwardly (for example, generally in a C-shape or a J-shape) from the toe region and the metatarsal region to a proximal end, which can be coupled directly or indirectly to a pylon.

SUMMARY

Prosthetic feet, especially the non-powered prosthetic feet, are typically designed for a specific activity, such as walking or running. The prosthetic feet experience a different type of (for example, lower) impact during walking than during running or sports activities. During running or sports activities, or any other activities with higher impact on the foot than during walking, the load experienced by the prosthetic foot can be up to three times a user's body weight. Current non-powered or mechanical prosthetic foot designs include a heel section and a toe section and are adapted for walking. Such feet designs may not be efficient beyond the intended activity. In some instances, greater bending of the foot and/or greater push-off force at the toe may be required when a person is engaged in certain activities (such as running) than during walking or standing. The standard walking feet may be too weak or may not absorb the higher impact during sports, such as running or jogging. On the one hand, it may not be safe or efficient to run or jog on a prosthetic foot designed for walking. Prosthetic feet designed for walking may perform poorly for running due to inadequate storage and release of energy produced during running (that is, inadequate impact absorption), and/or due to the foot being too weak to support the higher impact during running. On the other hand, running prosthetic feet can be different from walking prosthetic feet in several ways, for example, by not including a heel plate, or being set up taller than a walking foot due to the amount of compression required for running. The foot member of a prosthetic running foot is also much stiffer than the foot member of a prosthetic walking foot to accommodate the higher impact. It can be tiring or uncomfortable for a user to walk with a running prosthetic foot for daily use.

The user may need to switch to a different type of mechanical foot when engaging in different activities, for example, by wearing a prosthetic foot designed for daily use and switching to a prosthetic foot designed for running when participating in physical exercise, such as running. Moreover, the type of socket required for the different designs of the prosthetic foot may be different, making it more inconvenient to allow the user to switch between the different types of prosthetic feet for different activity levels.

The present disclosure provide a mechanical prosthetic foot with the ability to adjust the mechanical properties of two or more of areas of the prosthetic foot, for example, the heel region or the metatarsal region, based on the need of the user so that the user can use the same prosthetic foot for multiple activity levels (that is, different impact levels). The multiple activity levels can include at least running and walking.

A prosthetic foot of the present disclosure can include: an elongate sole member having a toe end defining a toe end of the prosthetic foot and a heel end defining a heel end of the prosthetic foot; a first upper member having a proximal end and a distal end and including a curve between the proximal and distal ends of the first upper member, the proximal end coupled to an adapter and the distal end coupled to the elongate sole member at an attachment location rearward of the toe end of the elongate sole member; and a second upper member having a proximal end and a distal end and including a curve between the proximal and distal ends of the second upper member, the proximal end of the second upper member coupled to the adapter and the distal end of the second upper member terminating near the attachment location, wherein the second upper member can be pre-compressed such that the distal end of the second upper member is biased toward the first upper member or the elongate sole member.

In some configurations, the first or second upper member can be generally C-shaped.

In some configurations, the foot can further include a first spacer between the distal ends of the first and second upper members.

In some configurations, the first spacer can be a single-piece spacer.

In some configurations, the first spacers can include an upper component and a lower component.

In some configurations, the distal end of the second upper member can be configured to slide along the first spacer during ambulation.

In some configurations, the first spacer can result in a gap between the first and second upper members along a portion of lengths of the first and second upper members, the gap being maintained throughout ambulation.

In some configurations, the gap can be further maintained by an adapter spacer between the proximal ends of the first and second upper members.

In some configurations, the foot can further include a second spacer between the distal end of the first upper member and the elongate sole member at or near the attachment location.

In some configurations, the foot can further include a heel bumper between the first upper member and the elongate sole member, the heel bumper located rearward of the attachment location.

In some configurations, the foot can further include a foam sheet extending from near the distal end of the first upper member along at least a partial length of the first upper member, the foam sheet being between the first upper member and the heel bumper.

In some configurations, the heel bumper can be generally wedge shaped, a thickness of the heel bumper being smaller at an anterior end than at a posterior end.

In some configurations, the heel bumper can include three stepped sections on a side facing the first upper member, wherein a posterior end of a first stepped section can be shorter than a posterior end of a second stepped section, and the posterior end of the second stepped section can be shorter than a posterior end of a third stepped section.

In some configurations, the first stepped section can be closer to the anterior end of the heel bumper and pre-compressed to minimize air gap between the heel bumper and the first upper member.

In some configurations, lengths of the first, second, and third stepped sections can be determined based on a position of the adapter, and wherein the position of the adapter can define a theoretical load line at ⅓ of a length of the prosthetic foot from the heel end.

In some configurations, the heel bumper can be made of foam.

In some configurations, the heel bumper can be 3D printed.

In some configurations, the 3D printed heel bumper can include a lattice structure.

In some configurations, the foot can further include a second heel bumper configured to be inserted between the first upper member and the heel bumper.

In some configurations, the second heel bumper can be inserted between the foam sheet and the heel bumper.

In some configurations, the second heel bumper can be removable.

In some configurations, the second heel bumper can be wedge-shaped.

In some configurations, the second heel bumper can comprise an internal cavity to receive a portion of the heel bumper.

In some configurations, the internal cavity can include one or more guide features configured to guide the second heel bumper onto the heel bumper.

In some configuration, the second heel bumper can be made of foam.

In some configurations, the second heel bumper can be 3D printed.

In some configurations, the foot can include a toe pad configured to be coupled to an underside of the elongate sole member at a toe region.

In some configurations, the foot can include a heel pad configured to be coupled to an underside of the elongate sole member at a heel region.

A prosthetic foot of the present disclosure can include: a first foot member having a proximal end and a distal end; a second foot member having a proximal end and a distal end, the proximal ends of the first and second foot members being coupled to an adapter, the adapter including an adapter spacer between the proximal ends of the first and second foot members; and a spacer between the distal ends of the first and second foot members, wherein the spacer and the adapter spacer can result in a gap between the first and second foot members along a portion of the length of the first and second foot members, the gap being maintained throughout ambulation, and wherein the distal end of the second foot member can be configured to slide over the spacer relative to the distal end of the first foot member.

In some configurations, the second foot member can be pre-compressed such that the distal end of the second foot member is biased toward the first foot member.

In some configurations, the foot can further include an elongate sole member having a toe end defining a toe end of the prosthetic foot and a heel end defining a heel end of the prosthetic foot, wherein the distal end of the first foot member can be coupled to the elongate sole member at an attachment location rearward of the toe end of the elongate sole member.

In some configurations, the distal end of the second foot member can terminate near the attachment location and wherein, during push off, the distal end of the second foot member can slide toward the toe end along the spacer to reduce a lever arm length of the second foot member.

In some configurations, the first spacer can be a single-piece spacer.

In some configurations, the first spacer can include an upper component and a lower component.

In some configurations, the foot can further include a second spacer between the distal end of the first foot member and the elongate sole member at or near the attachment location.

In some configurations, the foot can further include a heel bumper between the first foot member and the elongate sole member, the heel bumper located rearward of the attachment location.

In some configurations, the foot can further include a foam sheet extending from near the distal end of the first foot member along at least a partial length of the first foot member, the foam sheet being between the first foot member and the heel bumper.

In some configurations, the heel bumper can be generally wedge shaped, a thickness of the heel bumper being smaller at an anterior end than at a posterior end.

In some configurations, the heel bumper can include three stepped sections on a side facing the first upper member, wherein a posterior end of a first stepped section can be shorter than a posterior end of a second stepped section, and the posterior end of the second stepped section can be shorter than a posterior end of a third stepped section.

In some configurations, the first stepped section can be closer to the anterior end of the heel bumper and pre-compressed to minimize air gap between the heel bumper and the first foot member.

In some configurations, lengths of the first, second, and third stepped sections can be determined based on a position of the adapter, and wherein the position of the adapter defines a theoretical load line at ⅓ of a length of the prosthetic foot from the heel end.

In some configurations, the heel bumper can be made of foam.

In some configurations, the heel bumper can be 3D printed.

In some configurations, the 3D printed heel bumper can include a lattice structure.

In some configurations, the foot can further include a second heel bumper configured to be inserted between the first upper member and the heel bumper.

In some configurations, the second heel bumper can be inserted between the foam sheet and the heel bumper.

In some configurations, the second heel bumper can be removable.

In some configurations, the second heel bumper can be wedge-shaped.

In some configurations, the second heel bumper can comprise an internal cavity to receive a portion of the heel bumper.

In some configurations, the internal cavity can include one or more guide features configured to guide the second heel bumper onto the heel bumper.

In some configuration, the second heel bumper can be made of foam.

In some configurations, the second heel bumper can be 3D printed.

In some configurations, the foot can include a toe pad configured to be coupled to an underside of the elongate sole member at a toe region.

In some configurations, the foot can include a heel pad configured to be coupled to an underside of the elongate sole member at a heel region.

In some configurations, the first or second upper foot member can be generally C-shaped.

BRIEF DESCRIPTION OF THE DRAWINGS

These and other features, aspects, and advantages of the present disclosure are described with reference to the drawings of certain embodiments, which are intended to schematically illustrate certain embodiments and not to limit the disclosure.

DETAILED DESCRIPTION

The present disclosure provides examples of a prosthetic foot allowing a user to engage in different activity levels, for example, at least walking and running. Such a prosthetic foot can include a variety of features to improve adaptability of the prosthetic foot to different activity levels (and thus different loads or impacts), for example, by including two or more stiffness areas. The prosthetic foot disclosed herein can include a toe section and a heel section that can be soft enough for walking, but also exhibit stiffer properties during higher impact activities. The prosthetic foot disclosed herein may allow plantarflex more easily for a smoother rollover, but become increasingly or progressively stiffer during loading of the foot.

Figure 1:
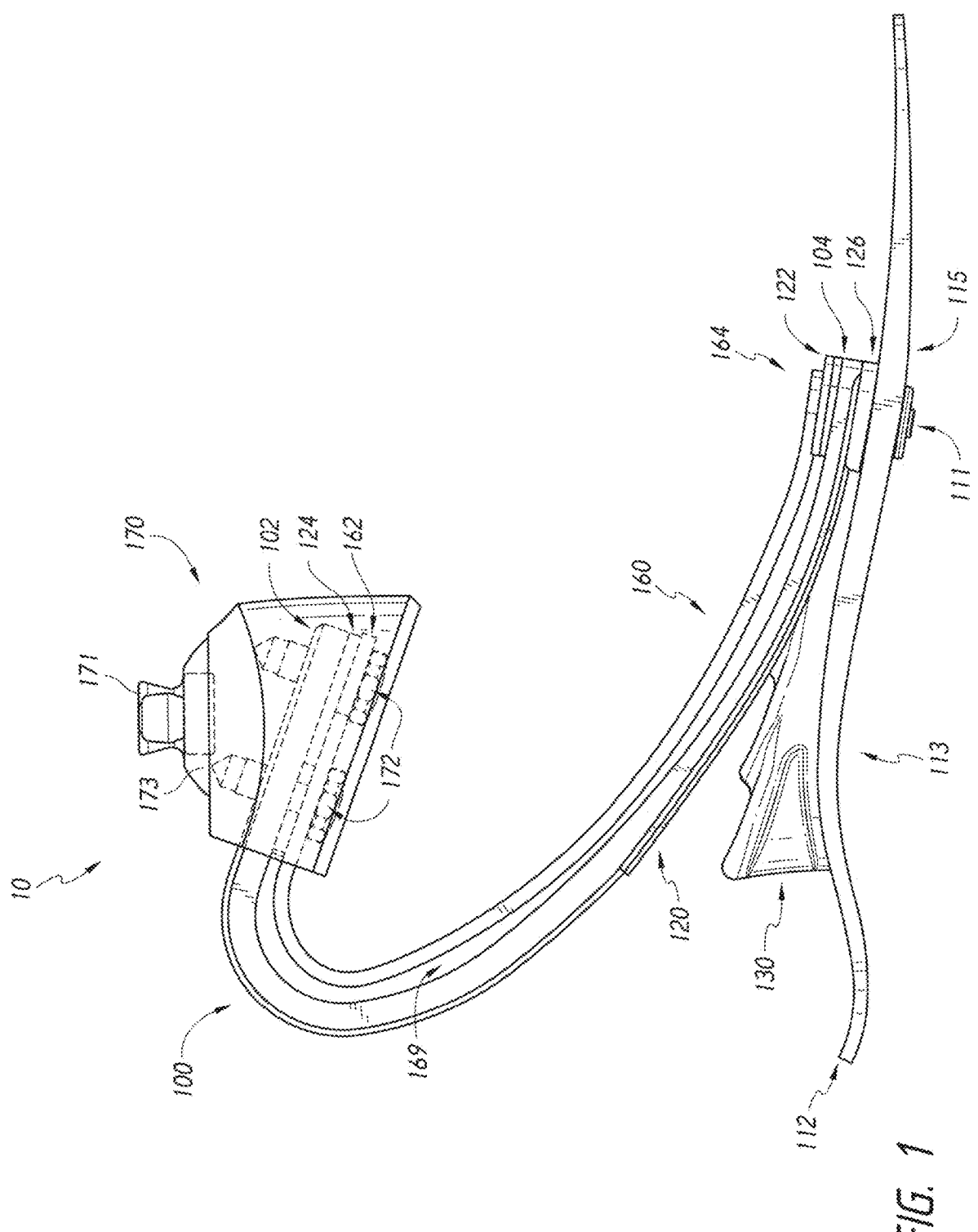
FIG. 1 illustrates an example mechanical prosthetic foot designed for multiple activity levels and including an elongate sole member, a first upper member, and a second upper member.

FIG. 1 illustrates an example prosthetic foot 10 of the present disclosure. Although the various features that allow the foot to be adapted for different activity levels are described with reference to FIG. 1, a prosthetic foot of the present disclosure may not need to include all the features and/or may include variations of certain features shown in FIG. 1, for example, the example prosthetic foot 16 as illustrated in FIGS. 16A-16G, 18A, and 18G. The prosthetic foot 10 can incorporate any of the features of the prosthetic foot 16 and the prosthetic foot 16 can incorporate any of the features of the prosthetic foot 10. Additionally, other prosthetic feet can include one or more of the features of the prosthetic foot disclosed herein to adapt for different activity levels. For example, a different prosthetic foot from the ones illustrated in FIGS. 1, 16A-16G, 18A, and 18H may incorporate a pre-compressed or pretensioned foot member described below.

As shown in FIGS. 1, 16A-16G, 18A, and 18H, the prosthetic foot 10, 16 can include an elongate sole member 110, a first upper foot member 100, and a second upper foot member 160. The sole member 110, the first upper foot member 100 and the second upper foot member 160 can be made of lightweight and rigid materials, such as one or more of graphite, fiberglass, carbon fiber, and the like. In some embodiments, the sole member 110, the first upper foot member 100 and the second upper foot member 160 can each be formed of multiple layers of material that define a monolithic piece.

The prosthetic foot 10, 16 can include the elongate sole member 110. The elongate sole member 110 can extend from a heel end 112 to a toe end 114. The heel end 112 can define a heel end of the prosthetic foot 10, 16. The toe end 114 can define a toe end of the prosthetic foot 10, 16. The elongate sole member 110 can include an arch region 113 between the heel end 112 and the toe end 114. For example, the arch region 113 can be at approximately the location of an arch of a natural human foot. The elongate sole member 110 can include a forefoot region 115 distal to the arch region 113 or between the arch region 113 and the toe end 114. The elongate sole member 110 can be curved upward in the arch region 113 relative to a remainder of the elongate sole member 110.

The first and second upper foot members 100, 160 can be located above the elongate sole member 110 when the foot 10, 16 is in a neutral or resting position on a flat surface. The first upper foot member 100 extends from a proximal end 102 to a distal end 104. The first upper foot member 100 can be generally curved from the proximal end 102 to the distal end 104. In the illustrated example, the first upper foot member 100 can be generally C-shaped. In other examples, the first upper foot member 100 may have other shapes. A portion of the first upper foot member 100 closer to the proximal end 102 can be coupled to an adapter 170. The adapter 170 can be a pyramid adapter as shown in FIGS. 1, 16A-16G, 18A, 18H, and 20, or any other suitable adapters.

The distal end 104 of the first upper foot member 100 can terminate proximal to the toe end 114 of the elongate sole member 110. The distal end 104 of the first upper foot member 100 can terminate distal to the arch region 113 of the elongate sole member 110. The distal end 104 of the first upper foot member 100 can terminate near or proximal to the forefoot region 115 of the elongate sole member 110. The first upper foot member 100 can be coupled (for example, fastened using a bolt 111 or any other suitable fastening mechanism) to the elongate sole member 110 near the distal end 104 of the first upper foot member 100.

The second upper foot member 160 can be located more anterior or forward than the first upper foot member 100. The second upper foot member 160 can extend from a proximal end 162 to a distal end 164. The second upper foot member 160 can have a shape that generally follows the shape of the first upper foot member 100. The second upper foot member 160 can be generally curved from the proximal end 162 to the distal end 164. In the illustrated example, the second upper foot member 160 can be generally C-shaped. In other examples, the second upper foot member 160 may have other shapes. A portion of the second upper foot member 160 closer to the proximal end 102 can be coupled to an adapter 170.

Proximal sections of the first upper foot member 100 and the second upper foot member 160 of the foot 10, 16 can angle downward toward the elongate sole member 110. The downward angling of the proximal sections can allow the foot 10 to be oriented better for running motion. The effective lever arm of the foot 10, 16 extends from the toe end of the foot 10 to a point furthest away, and is therefore longer, than if the proximal sections are generally horizontal. The downward angle of the proximal sections can also reduce a build height of the prosthetic foot 10, 16 than if the proximal sections are generally horizontal.

Figure 2A:
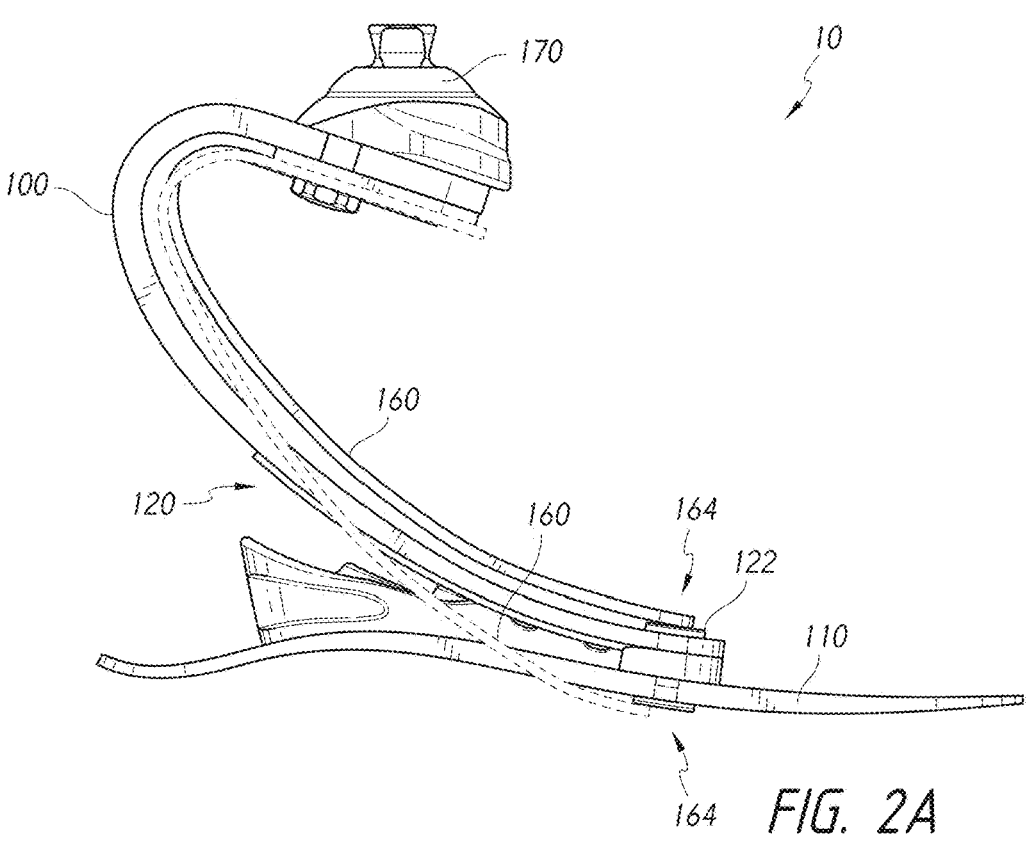
FIG. 2A illustrates an example prosthetic foot with a loaded second upper member and an unloaded second upper member.
Figure 2B:
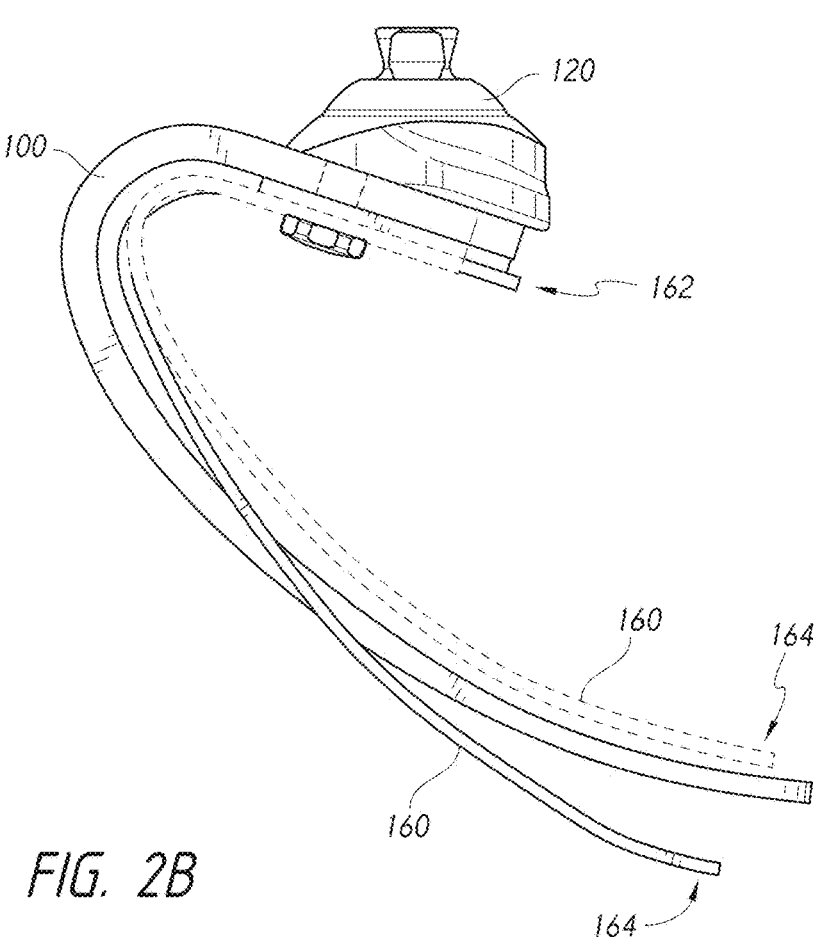
FIG. 2B illustrates an example prosthetic foot with the second upper member in an unloaded state and a loaded state.

The second upper foot member 160 of the foot 10, 16 can be a pre-compressed foot member. As shown in FIGS. 2A and 2B, the second upper foot member 160 in its free, unloaded state would have its distal end 164 extend below the first upper foot member 100. The prosthetic foot in FIG. 2A can be the same foot as the prosthetic foot 10 as shown in FIG. 1, or a different prosthetic foot that includes similar components as the prosthetic foot 10. In some examples, the second upper foot member 160 in its free, unloaded state would have its distal end 164 extend below the elongate sole member 110. With the proximal end 162 fixedly coupled to the adapter 170, the distal end 164 of the second upper foot member 160 can be compressed toward the proximal end 162 during assembly of the prosthetic foot 10, 16, such that the distal end 164 of the pre-compressed second upper foot member 160 is biased toward the first upper foot member 100 and/or the elongate sole member 110. Accordingly, the pre-compressed second upper foot member 160 is longer than if a non-compressed foot member were to be placed anterior to the first upper foot member 100. Because of its length, the pre-compressed second upper foot member 160 also bends the C-shaped first upper foot member 100 more backward and upward, that is, pulling the C-shape more open than an unloaded second upper foot member. The more backward and upward bending can have an effect on heel strike (e.g., by absorbing more impact) and when the foot 10, 16 plantarflexes (for example, by making plantarflexion easier for the foot 10, 16). The backward and upward bending can also cause the first upper foot member 100 to influence the motion of the foot 10, 16, for example, by interacting more with a foam sheet 120 (which will be described in more detail below) during walking (e.g., the stance phase). Using the pre-compressed second upper foot member 160 to tension the first upper foot member 100 can also tension the entire prosthetic foot 10, 16, that is, all the components with spring properties can become pretensioned.

Optionally, the prosthetic foot may not include the elongate sole member 110 and may include just a first foot member 100 and a second foot member 160 as shown in FIG. 2B. Such a prosthetic foot can include a spacer 122 (as shown in FIGS. 1 and 2A) between the first and second foot members 100, 160 at or near the distal end of the second foot member 160. The second foot member 160 can be precompressed as described above. Optionally, a prosthetic foot can include any features of the foot 10 in FIG. 1 or the foot 16 in FIG. 16A or 18A except that the elongate sole member 110 and the heel bumper 130 (which will be described in greater details below) can be replaced by a heel plate extending from a location generally aligned with the adapter 170, or more anterior than the anterior end of the adapter 170, to a heel end of the foot 10 and that the distal end 104 of the first foot member 100 can be extended to a toe end of the foot (that is, the distal end 104 of the first foot member 100 can terminate distally or slightly anterior of the distal end 164 of the second foot member 160) to provide proper rollover. The heel plate can curve upward at an arch region of the foot.

Figure 16A:
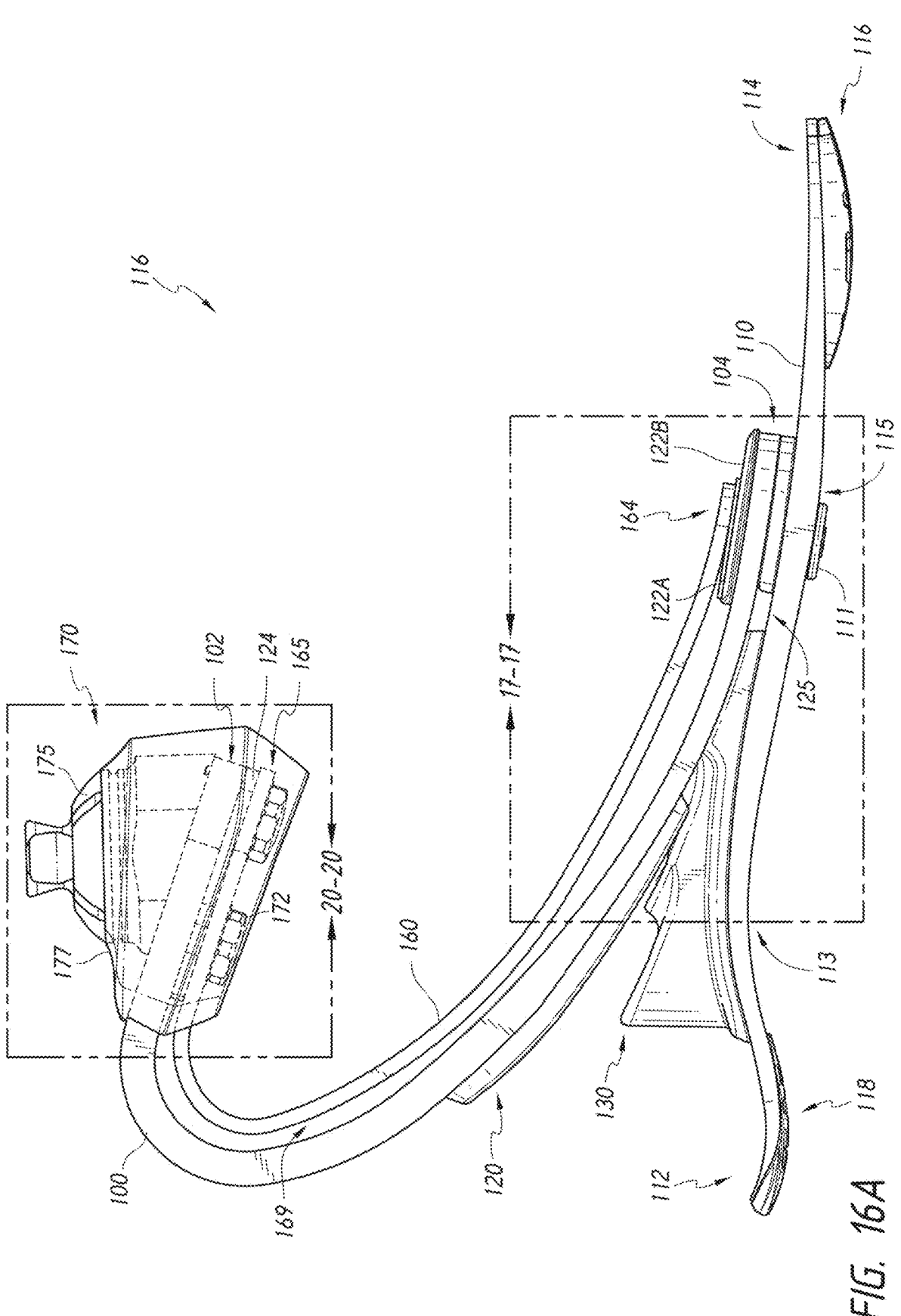
FIG. 16A illustrates a side view of an example mechanical prosthetic foot designed for multiple activity levels and including an elongate sole member, a first upper member, and a second upper member.
Figure 16B:
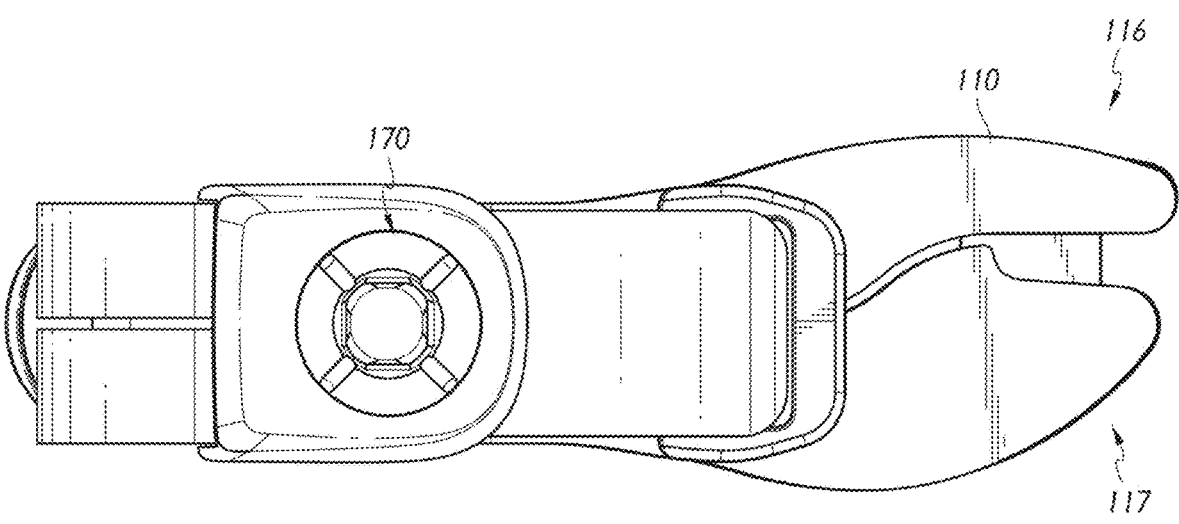
FIG. 16B illustrates a top view of the foot shown in FIG. 16A.
Figure 16C:
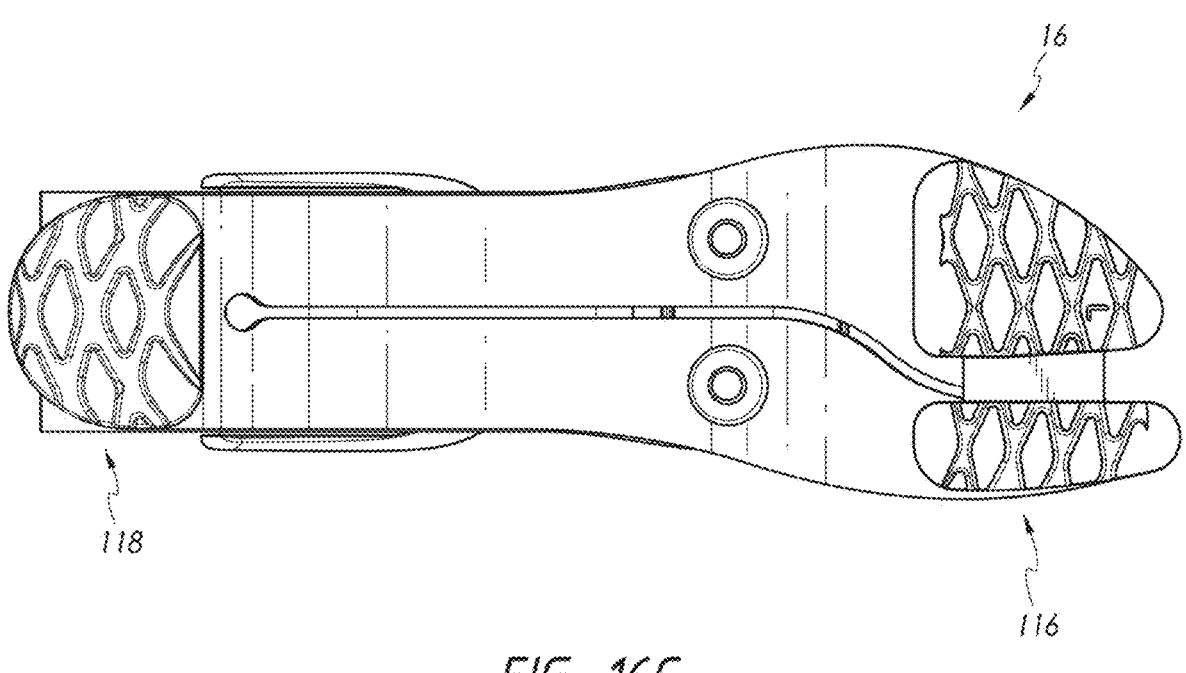
FIG. 16C illustrates a bottom view of the foot shown in FIG. 16A.
Figure 16E:
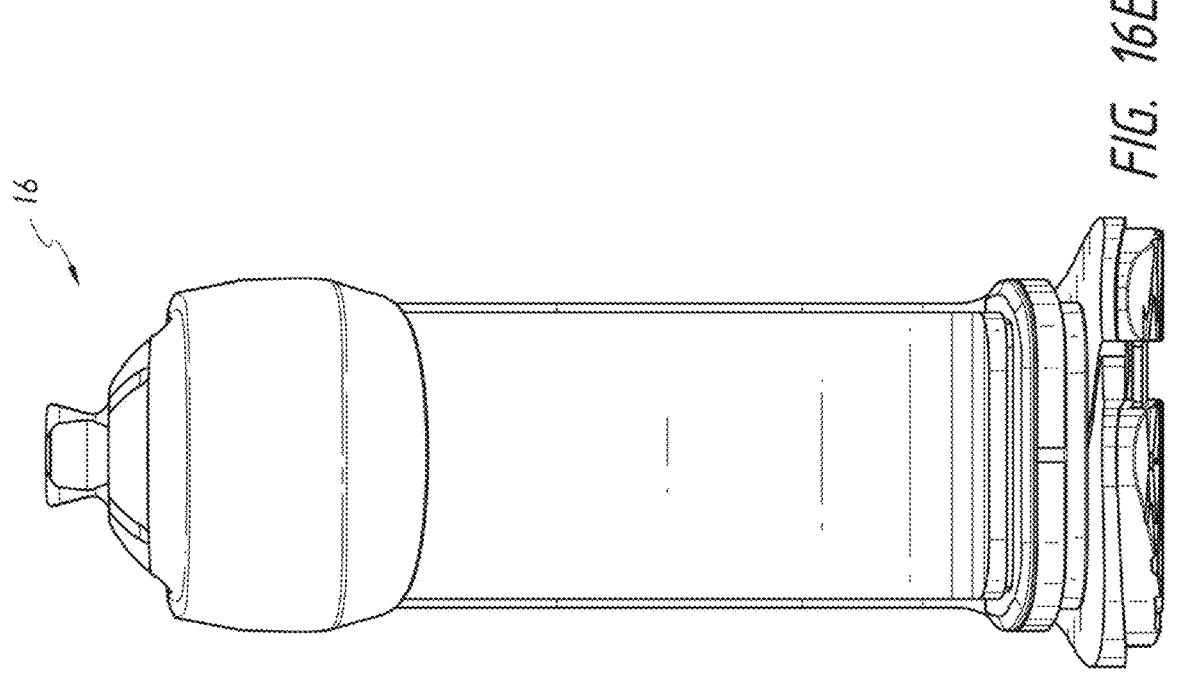
FIG. 16E illustrates a back view of the foot shown in FIG. 16A.
Figure 16D:
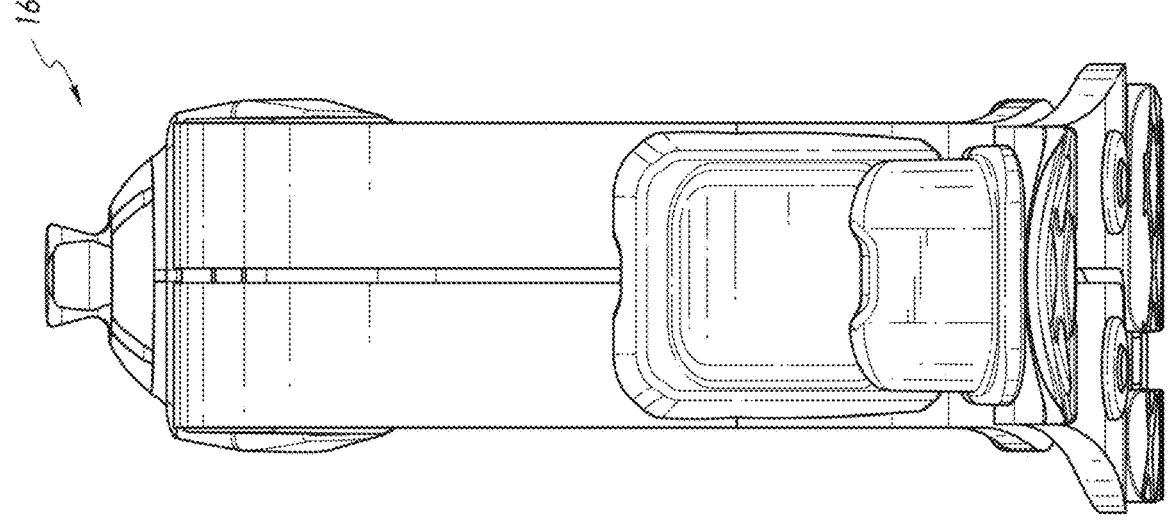
FIG. 16D illustrates a front view of the foot shown in FIG. 16A.
Figure 16F:
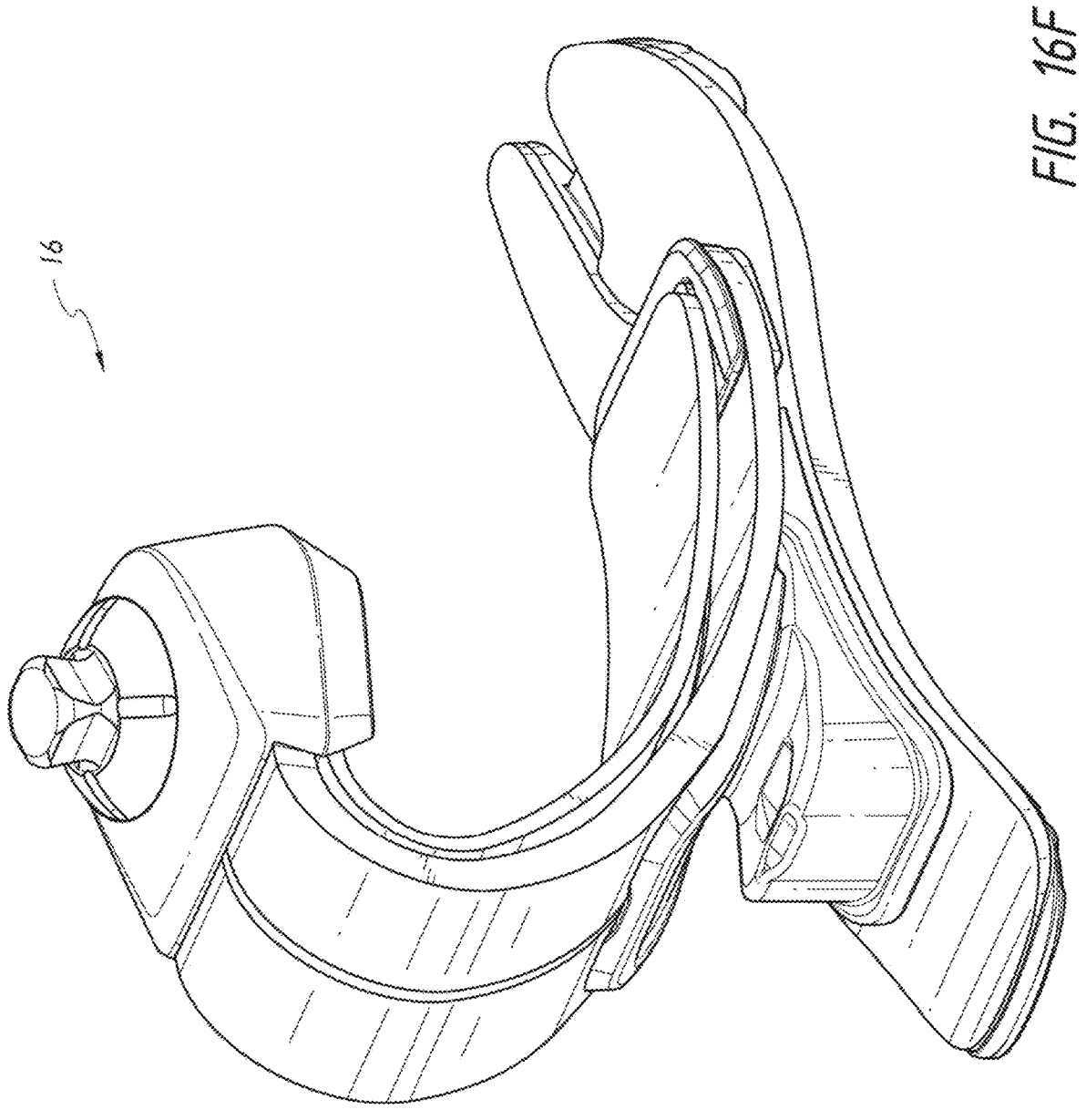
FIG. 16F illustrates a back perspective view of the foot shown in FIG. 16A.
Figure 16G:
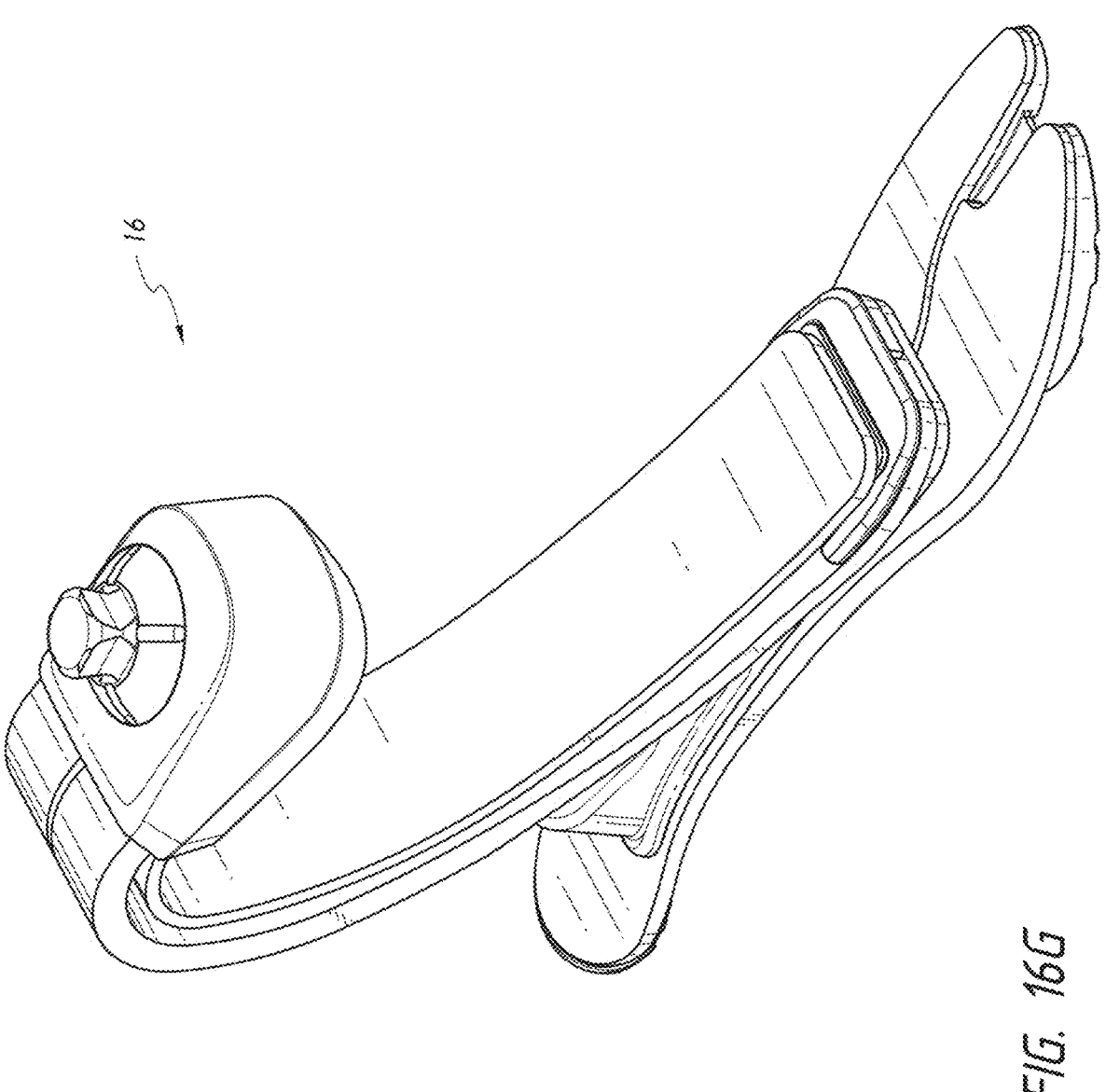
FIG. 16G illustrates a front perspective view of the foot shown in FIG. 16A.
Figures 18A, 18B:
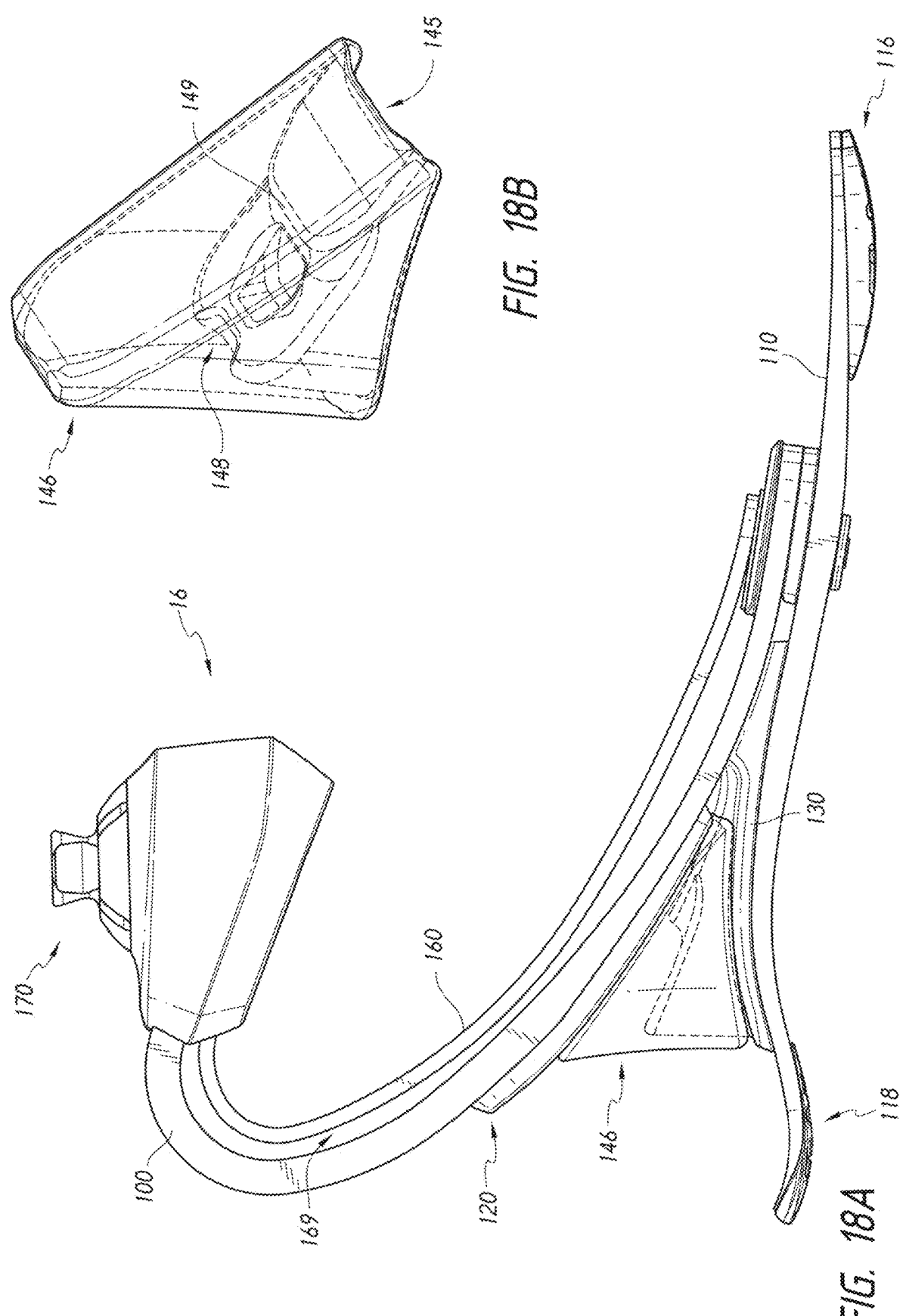
FIG. 18A illustrates the foot of FIG. 16A with an example removable second heel bumper.
FIG. 18B illustrates a perspective view of the second heel bumper shown in FIG. 18A.

Optionally, a prosthetic foot can include any features of the foot 10 in FIG. 1 or the foot 16 in FIG. 16A or 18A except that the elongate sole member 110 and the heel bumper 130 can be replaced by a different heel bumper under the first upper foot member 100 and that the distal end 104 of the first foot member 100 can be extended to a toe end of the foot. The heel bumper can have generally a wedge shape. A top surface of the different heel bumper, which is the surface that contacts the first foot member, can be generally forwardly-facing concave to match a shape of a curved section of the first member 100. A bottom surface of the different heel bumper can be generally level with a bottom surface of the toe of the first foot member when the prosthetic foot is at rest. Therefore, the bottom surface of the different heel bumper and the bottom surface of the toe section of the first foot member can contact a ground surface when the prosthetic foot is in use. The length of the different heel bumper can vary. The different heel bumper can have a distal end at or near the distal section of the first foot member. The different heel bumper can have a heel end that can be more posterior than the adapter or approximately aligned with a posterior end of the adapter 170 when the prosthetic foot is at rest. The different heel bumper can have a stiffness or be made of the same material as the heel bumper 130 disclosed herein.

In the illustrated examples, the distal end 164 of the second upper foot member 160 is not fixed, and can move freely to adjust a lever arm of the foot 10, 16 during ambulation. Optionally, the distal end 164 of the second upper foot member 160 can be fixed, for example, to the bolt 111. Letting the distal end 164 of the second upper foot member 160 move freely can improve dynamics of the foot 10, 16. For example, the lever arm can be shortened from midstance to toe-off. The sliding of the distal end 164 of second upper foot member 160 can therefore improve push-off and add dynamics properties to the foot 10, 16. During loading of the foot 10, 16, the lever arm of the second upper foot member 160 shortens as the distal end 164 of second upper foot member 160 moves forward, which can progressively increase the stiffness of the foot 10, 16. For example, at heel strike or when the foot 10, 16 dorsiflexes, the foot 10, 16 can become stiffer to absorb the impact.

The prosthetic foot 10, 16 can optionally further include more than one upper foot member located anterior to the first upper foot member 100. One or more of these additional upper foot members may be pre-compressed as described above.

The improved mechanical properties of the prosthetic foot disclosed herein, such as the foot 10, 16, by including the pre-compressed second upper foot member 160 have been demonstrated in various mechanical testing, which are illustrates in FIGS. 3-7B.

Figure 3:
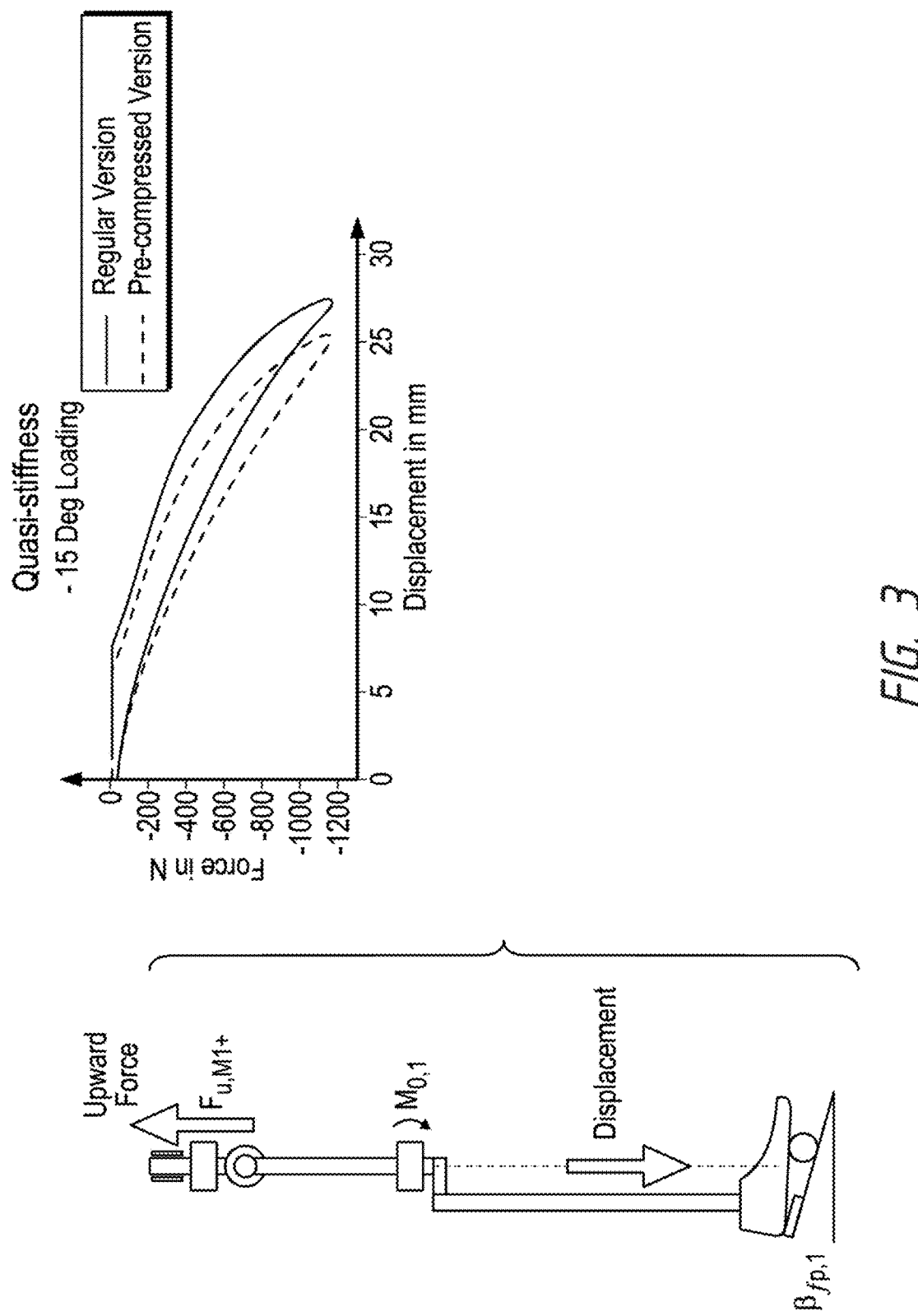
FIG. 3 illustrates a static quasi-stiffness test setup for the prosthetic foot of FIG. 1 and exemplary test results.

As shown in FIG. 3, a static loading test with the jig as shown in FIG. 3 was used to test two prosthetic feet with mechanically the same components except that the second upper foot member in one foot is not pre-compressed (labeled as "Regular version" in the Quasi-stiffness graph of FIG. 3) and the second upper foot member in the other foot is pre-compressed as described above (labeled as "Pre-compressed version" the Quasi-stiffness graph of FIG. 3). The tests involved static loading and unloading of the heel under different floor angles and full roll-over from heel-to-toe, simulating different body weights (70 kg to 100 kg).

The graph in FIG. 3 is an exemplary force vs. displacement graph at −15 degree floor angle. Although not shown, the test data obtained at other floor angles exhibit similar trends. The graph has been post-processed by using sensor data of the loading machines or cameras directed at the prosthetic foot under loading. The blue curve represents the force vs. displacement relationship of the Regular version and the red curve represents the force vs. displacement relationship of the Pre-compressed version. As shown in the graph, there is greater vertical displacement of the foot of the regular version than the pre-compressed version under the same loading conditions. That is, the foot of the regular version exhibits lower stiffness at the toe and the heel of the foot than the foot of the pre-compressed version. The static test shows that the pre-compressed second upper foot member 160, although pivoting at its distal end 164 closer to the toe end than the heel end of the prosthetic foot 10, 16, also can influence the behavior and stiffness of the heel of the prosthetic foot 10, 16.

The static test also shows that the foot of the pre-compressed version shows similar displacement as the foot of the regular version when loading at the toe (with the foot resting plat on a foot platform). In addition, the midfoot displacement of the foot of the regular version indicates slightly more plantarflexed alignment than the foot of the pre-compressed version.

Figure 4:
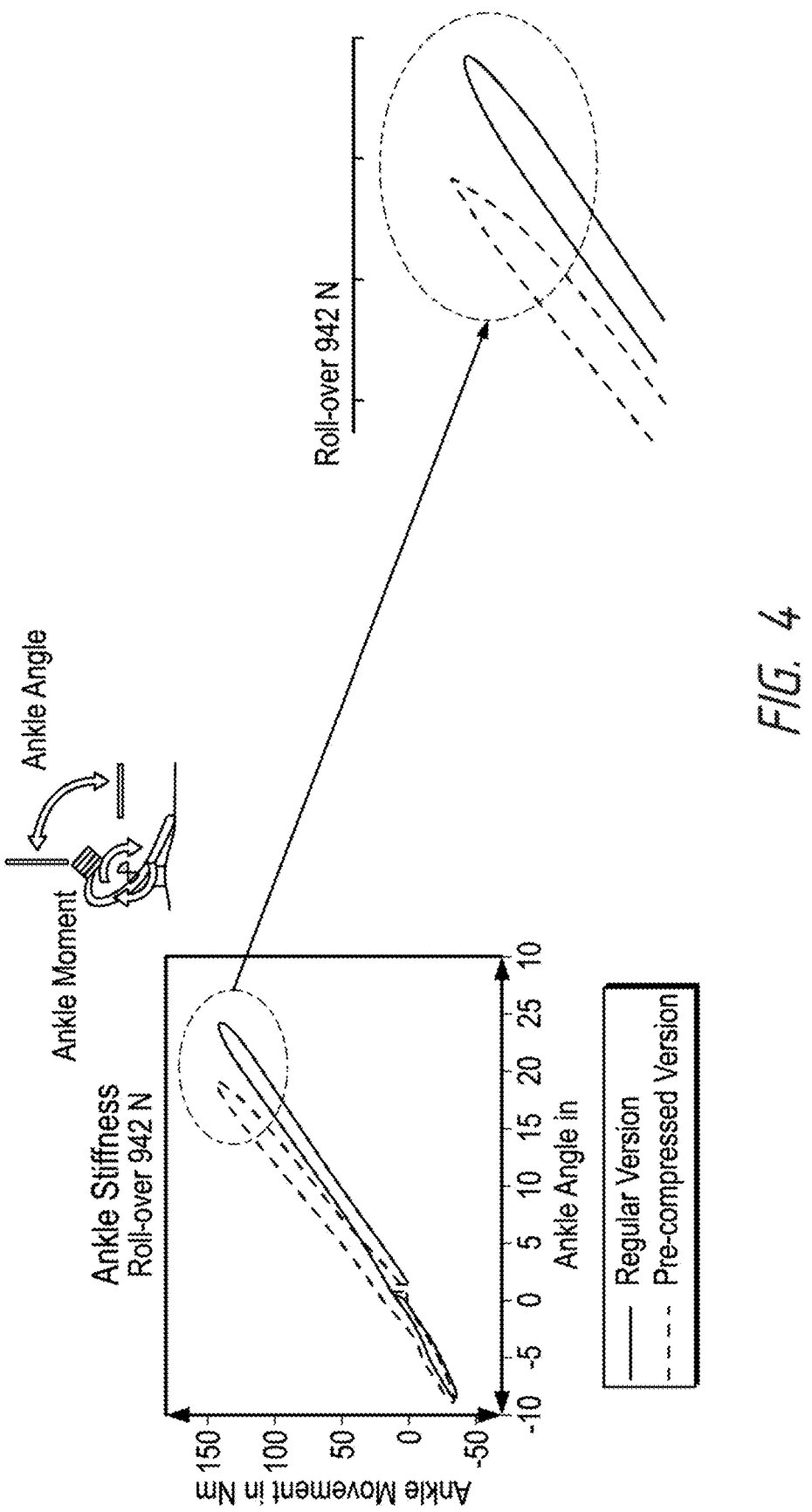
FIG. 4 illustrates a dynamic heel-to-toe rollover test setup for the prosthetic foot of FIG. 1 and exemplary test results.
Figure 5A:
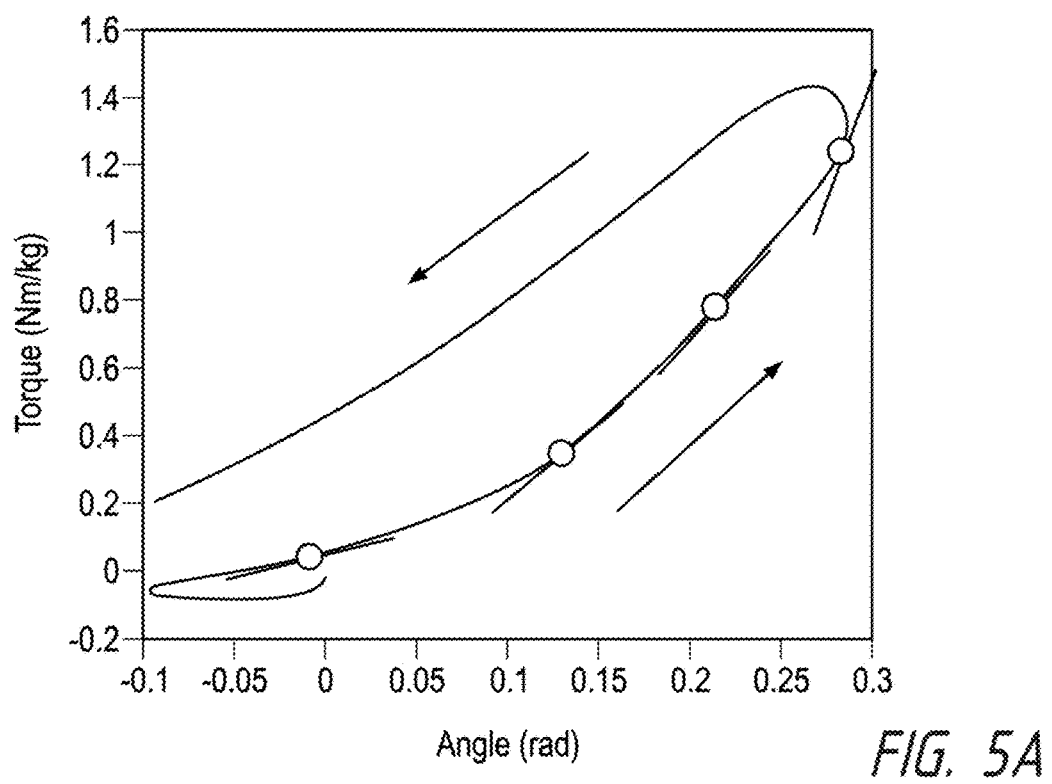
FIGS. 5A-5B are graphs of exemplary human ankle stiffness data.
Figure 5B:
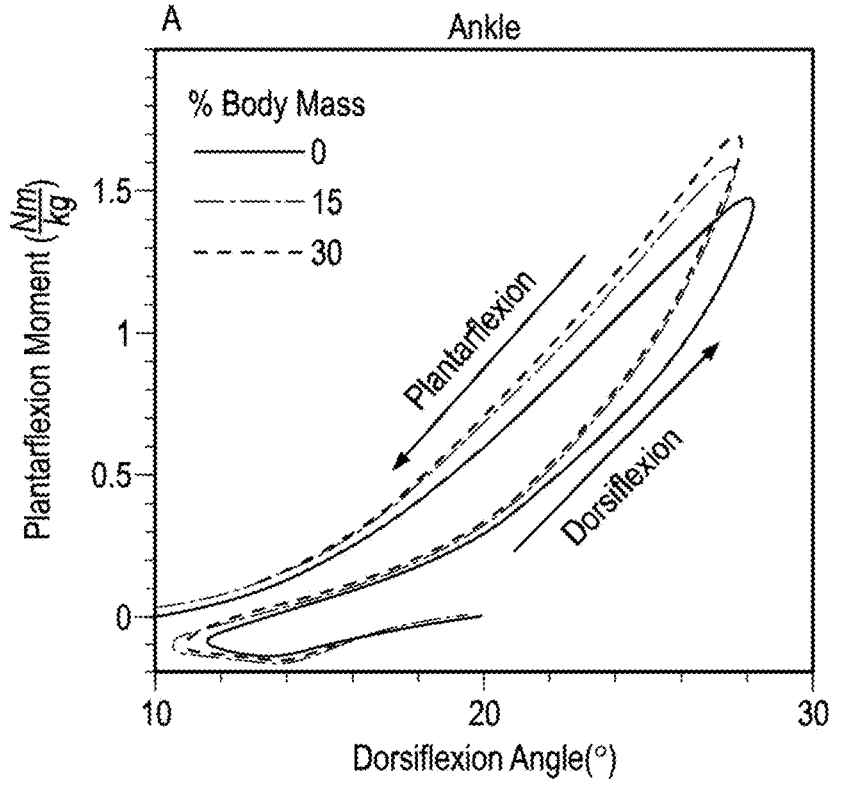

FIG. 4 shows a testing jig for roll-over testing (testing heel-to-toe motion under dynamic load) of the foot of the regular version and the foot of the pre-compressed version, respectively. The graph shows an exemplary relationship of the ankle moment vs. ankle angle under a certain roll-over load. Data obtained at other loads exhibit similar trends as shown in FIG. 4. The foot of the regular version has the same ankle stiffness at plantarflexion and dorsiflexion. In addition, the ankle range of motion may be too high in dorsiflexion for the foot of the regular version. In contrast, the foot with the pre-compressed second upper foot member (that is, the pre-compressed version) exhibits less total range of motion, with the range of motion mainly originating from dorsiflexion (closer to the human model as shown in FIGS. 5A-5B). The travel of dorsiflexion is more limited despite the foot of the pre-compressed version having a soft toe. Although the pre-compressed version exhibits a similar ankle stiffness in plantarflexion as the regular version, the pre-compressed second upper foot member stiffens the forefoot while the foot is rolling over (rising moment at −4°) with progressive loading. The pre-compressed second upper foot member can be engaged during rollover before midstance. Accordingly, the overall forefoot stiffness is higher and there is higher ankle stiffness at dorsiflexion than at plantarflexion compared to the regular version. In other words, the pre-compressed second upper foot member allows for different stiffness of the foot at plantarflexion and dorsiflexion. As shown in the graph in FIG. 4, the hysteresis of the toe in the pre-compressed version is smaller under all loads, which means there is more energy return at push off. Although the forefoot stiffness (at dorsiflexion) is higher, the heel stiffness (at plantarflexion) is not affected in the foot of the pre-compressed version. This variable stiffness property is more desirable than increasing the overall stiffness of the foot members when the toe stiffness and the heel stiffness are both increased, which would make the foot less suitable for walking.

The roll-over test shows that the prosthetic foot with the pre-compressed second upper foot member can behave more like the natural human ankle in its variable stiffness property. FIG. 5A illustrates an average torque-angle relationship of a natural human ankle (Rouse et al. 2014). The quasi-stiffness value of the human ankle can be calculated as the slope (denoted by thin black lines) of the relationship at each time point (denoted by a dot). The graph in FIG. 5A allows for estimation of the human ankle impedance during stance phase of walking. FIG. 5B illustrates human ankle joint quasi-stiffness during walking with added mass (Kern et al. 2019). The slope of each linear fit in the graphs can be interpreted as the quasi-stiffness value. As shown in FIGS. 5A and 5B, the human ankle has a soft heel at plantarflexion. During rollover, the calf muscles start to stiffen the ankle joint, resulting in progressively higher stiffness in dorsiflexion.

Figure 6:
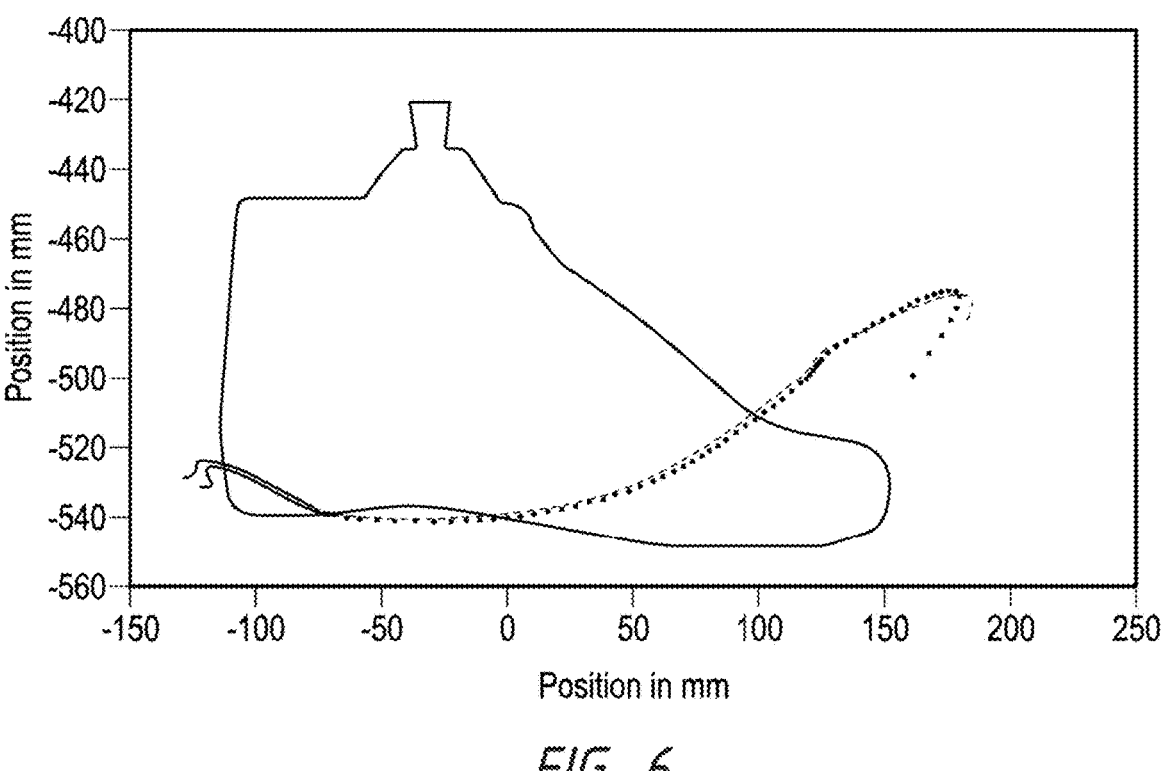
FIG. 6 illustrates a roll-over profile of the prosthetic foot of FIG. 1 under certain load conditions.

FIG. 6 illustrates an exemplary roll-over shape of the foot of the regular version (blue curve) and the foot of the pre-compressed version (red curve). The graphs in FIG. 6 depict changes in the foot roll-over radius when rolling from heel-to-toe. The trend shown in FIG. 6 is similar to the trends described above with data in FIGS. 3 and 4. Compared to the regular version, the foot with the pre-compressed second upper foot member (for example, the foot 10, 16) initiates heel strike smoother by deforming less while providing the same ankle motion as the regular version. The foot with the pre-compressed second upper foot member also keeps load at the toe at higher level for longer, providing greater and longer support at push off. The foot with the pre-compressed second upper foot member provides a different stiffness (that is, a soft heel and a stiffer toe), and limits the ankle range of motion. Overall, the foot with the pre-compressed second upper foot member exhibits a smoother (transition time from heel to toe) rollover shape. Although the pre-compressed second upper foot member behaves stiffer, it does not alter the overall curvature of the rollover shape. In contrast, a foot member with an overall greater stiffness would flatten the rollover radius, making rollover less smooth.

Figure 7A:
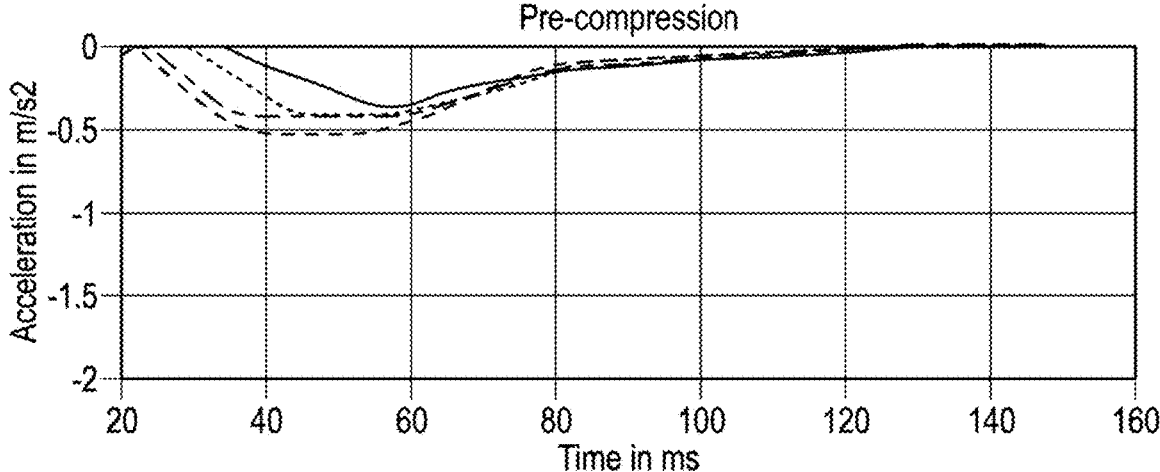
FIGS. 7A-7B illustrate acceleration and velocity data of the prosthetic foot of FIG. 1 (7A) and another prosthetic foot without a pre-compressed second upper member (7B) under similar load and displacement conditions.
Figure 7B:
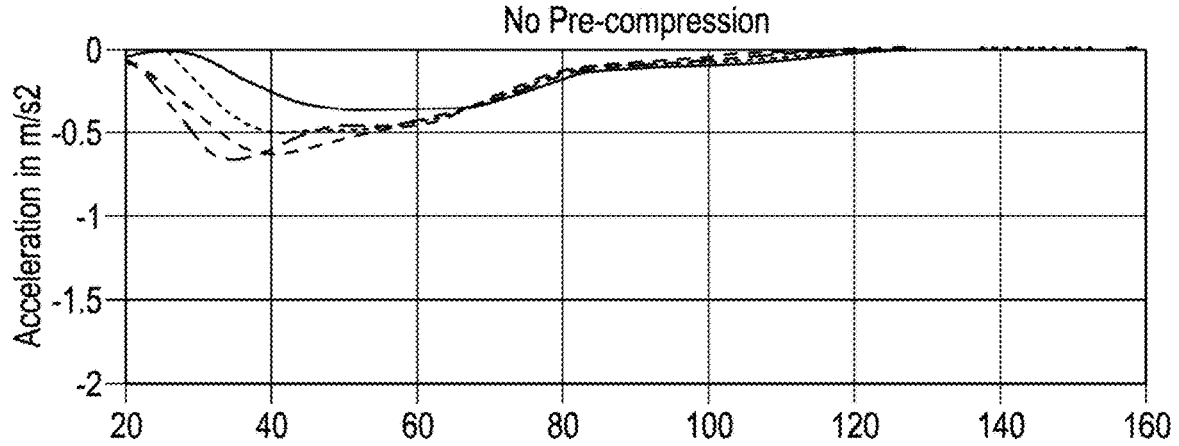

Impact data during heel strike is shown in FIGS. 7A and 7B. FIGS. 7A-7B illustrate acceleration data of the prosthetic foot of the pre-compressed version (FIG. 7A), which may be, for example, the foot 10, 16, and the prosthetic foot of the regular version (FIG. 7B) under similar load and displacement conditions. In each of FIGS. 7A and 7B, the graph shows curves for different impact loads from 70 kg (full line) to 100 kg (dotted line). The loading (for example, at heel strike) are very similar during the first milliseconds of stance of the feet with or without the pre-compressed second upper member. However, as shown in the graph of each of FIGS. 7A and 7B, the foot of the regular version experiences a higher impact, as the first upper foot member 100 needs to be bent more into plantarflexion of the foot from relaxed state. For the pre-compressed version, even during higher loads there is greater impact absorption and a smoother impact, as the first upper foot member 100 is already pre-bent by the pre-compressed second upper foot member 160 as describe above, and the foot can plantarflex easier with a lower initial force.

Figure 17:
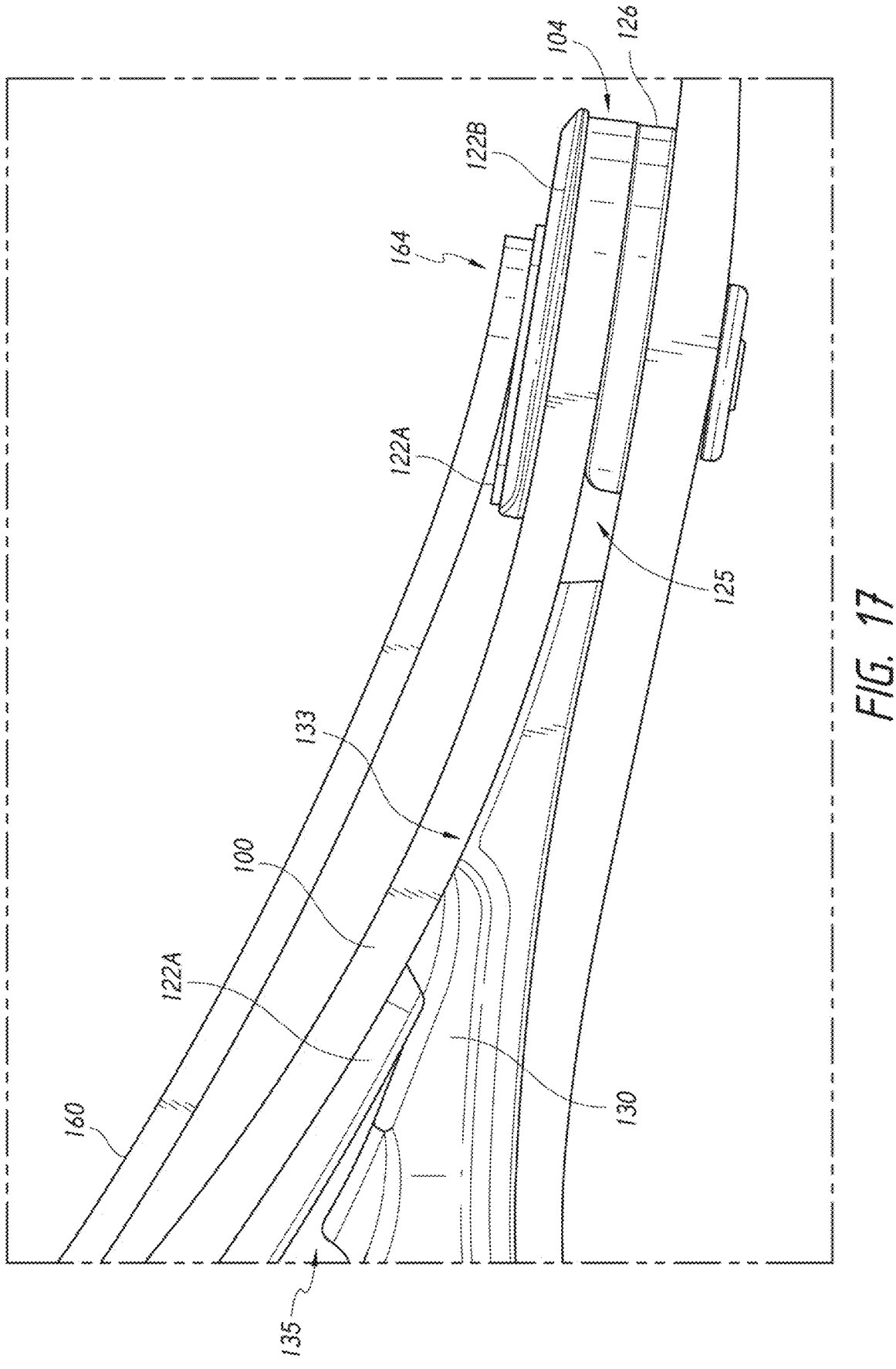
FIG. 17 illustrates a first detailed view of the foot shown in FIG. 16A.

The prosthetic foot 10, 16 can include a spacer to facilitate sliding of the distal end 164 of the pre-compressed second upper foot member 160. As shown in FIG. 1, the prosthetic foot 10 can include a single first spacer 122 between the distal ends 104, 164 of first upper foot member 100, second upper foot member 160. The single first spacer 122 can overlap with an entire distal region of the first upper foot member 100. The single first spacer 122 can extend up to the distal end 104 of the first upper foot member 100. The single first spacer 122 can cover an entire head of the bolts 111. As shown in FIGS. 16A and 17, the prosthetic foot 16 can include a two-part first spacer, which can include an upper portion 122A and a lower portion 122B. The lower portion 122B can overlap with an entire distal region of the first upper foot member 100. The lower portion 122B can extend up to the distal end 104 of the first upper foot member 100. The lower portion 122B can cover an entire head of the bolts 111. The upper portion 122A may not necessarily have the same dimensions and/or shape as the lower portion 122B, or cover the same area as the lower portion 122B. For example, the upper portion 122A can be thinner than the lower portion 122B, such as by at least 50%. As another example, the upper portion 122A can terminate more proximal than the distal end 104 of the first upper foot member 100. The upper portion 122A may not necessarily cover the entire head of the bolts 111.

The first spacer can be used to affect the stiffness change of the foot 10, 16. The material of the single first spacer 122 or at least the upper portion 122A (and also optionally the lower portion 122B) of the two-part first spacer can be slippery (that is, having low friction coefficient), thereby facilitating the distal end 164 of the second upper foot member 160 to slide along the first spacer 122 during rollover. The single first spacer 122 or the upper and/or lower portions 122A, 122B of the two-part first spacer may be made of or at least include foam. The single first spacer 122 or the upper and/or lower portions 122A, 122B of the two-part first spacer can be a pad made of soft foam (for example, expanded thermoplastic urethane (eTPU) pad). The foam pad can work in the extension direction (connected to both sides or one side). The single first spacer 122 or the upper and/or lower portions 122A, 122B of the two-part first spacer can alternatively include a spacer fabric, 3D printed lattice, a stiff, compression limiting material (for example, like a comb) that shears in the direction of the movement of the distal end 164 of the second upper foot member 160.

Alternatively, the first spacer 122 can include roller(s). The second upper foot member 160 can move over the roller(s), which can keep the contact point more defined and allow the second upper foot member 160 to return to its original position more quickly. The first spacer 122 can also include a spring. The spring can be mounted to the lateral sides of the second upper foot member 160.

Figure 23A:
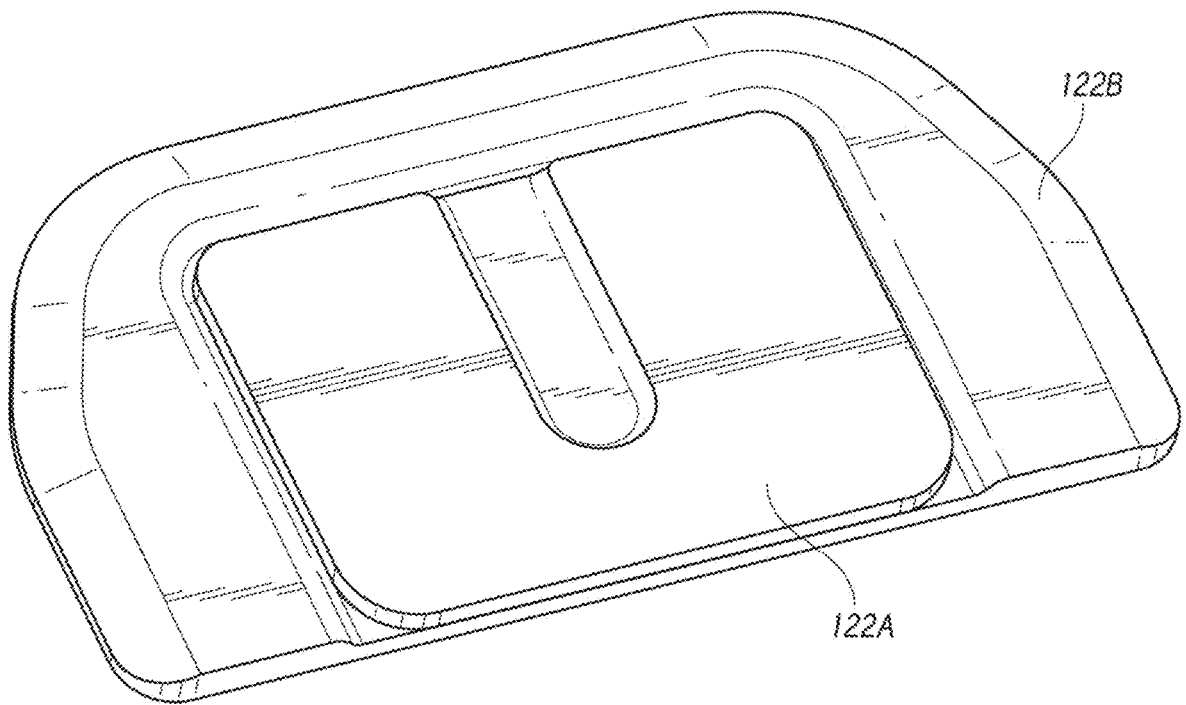
FIG. 23A illustrates an example two-part spacer of the prosthetic foot in FIG. 16A.

To reduce friction, the upper portion 122A can be made of a Teflon pad or a foam pad over the lower portion 122B, which may be, for example, a plastic spacer. The Teflon or foam pad has low friction and can allow quick return of the second upper foot member 160 to its original position. When rolling to the toe of the foot, the second upper foot member 160 can move further, allowing for a softer toe. FIG. 23 illustrates a non-limiting example of the two-part spacer having an upper portion 122A and a lower portion 122B. The upper portion 122A can be made of, for example, a foam material. The lower portion 122B can be made of, for example, a plastic material or any other material that is stiffer than the foam material. The upper portion 122A can provide friction to the second upper member 160, while the lower portion 122B can provide support to the upper portion 122A. In this way, the friction and support of the two-part spacer can remain the same over a composite surface below the spacer. For example, the composite surface can include at least heads of the bolt 111 and the first upper member 100. In the illustrated example, the upper portion 122A can have a U-shape or a horseshoe shape, with the lower portion 122B have a corresponding recess to receive the upper portion 122A. The upper portion 122A can be of any other suitable shapes. The upper portion 122A can be surrounded by the lower portion 122B on one or more sides of the upper portion 122A. The recess on the lower portion 122B can have a depth to surround a partial height of the upper portion 122A. Additionally, the second upper member 160 can include a polyethylene (PE) film covering or being integrated into the carbon fibers. The PE film can reduce wear of the second upper member 160 and increase friction with the upper portion 122A. The increased friction can remain the same in different environments, for example, in conditions that are wet, dry, cold, warm, and/or in sand, while minimizing noise when the second upper member 160 slides over the upper portion 122A.

Figure 8:
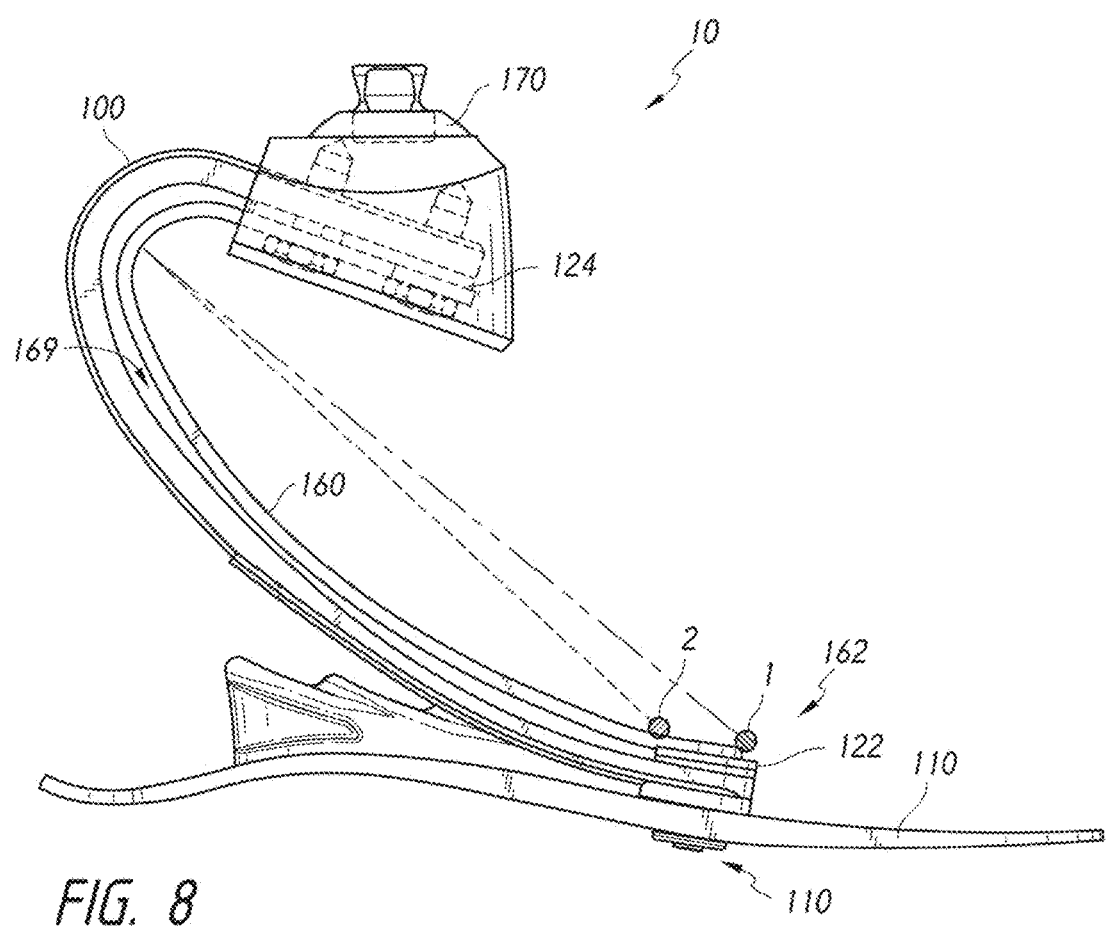
FIG. 8 illustrates example sliding contact of the second upper member at different gait stages.
Figure 9B:
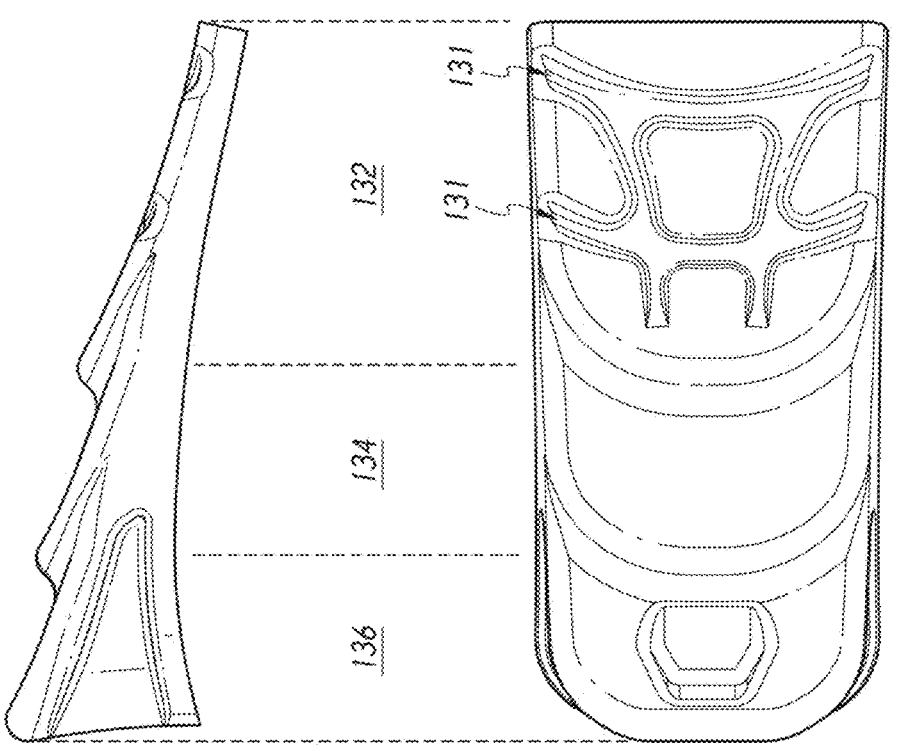
FIGS. 9A-9B illustrate perspective, side, and top views of a stepped heel bumper of the prosthetic foot of FIG. 1.
Figure 9A:
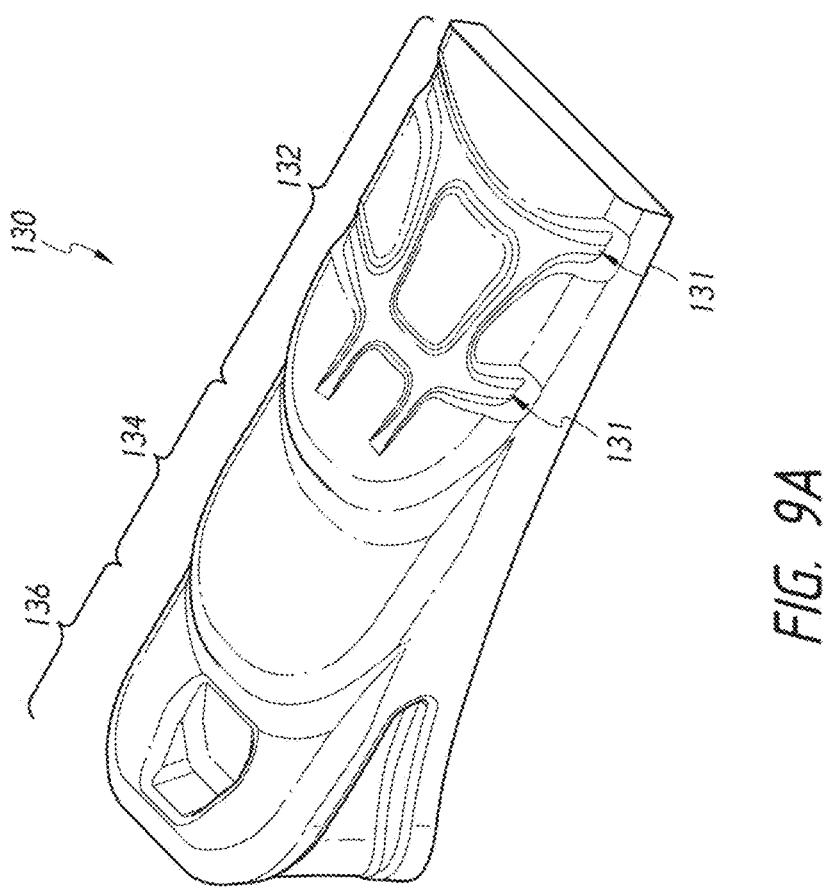

The single first spacer 122 and the two-part first spacer 122A, 122B, and/or a multi-part spacer can provide substantially the same function to the prosthetic foot, 10, 16, including for example, the same sliding characteristics between the second upper foot member 160 and the first spacer 122, 122A, 122B. When the foot 10, 16 transitions from heel to toe during rollover, the energy is stored in the pre-compressed second upper foot member 160. In particular, the energy is stored in the second upper foot member 160 with the contact point between the second upper foot member 160 and a remainder of the foot 10, 16 (for example, the single first spacer 122 or the upper portion 122A of the two-part first spacer) at a more distal location along the length of the second upper foot member 160 due to the additional length of the pre-compressed second upper foot member 160 as described above. FIG. 8 illustrates contact points on the second upper foot member 160 during different gait stages. In FIG. 8, Point 1 is a contact location during initial loading of the second upper foot member 160. Point 1 is a more anterior location than Point 2. The resultant lever arm is shown as the red broken line. The energy is stored in a long lever arm (that is, easier to bend) at Point 1. As the foot 10, 16 rolls over, the distal end 164 of the second upper foot member 160 slides over the single first spacer 122 or the upper portion 122A of the two-part first spacer toward the toe end of the foot 10, thus making the effective lever arm of the second upper foot member 160 shorter. This is because as the distal end 164 of the second upper foot member 160 moves more distally or anteriorly toward the toe end of the foot 10, the point of contact between the second upper foot member 160 and the single first spacer 122 or the upper portion 122A of the two-part first spacer moves more proximally along the length of the second upper foot member 160. For example, the lever arm (illustrated as the yellow broken line) may shorten up until the point contact slides to about Point 2 as shown in FIG. 8. Point 2 illustrates a loading point during toe off. When the lever arm has become shorter, the second upper foot member 160 becomes stiffer. The stored energy can be released from the second upper foot member 160 when having a shorter lever arm, thus providing a greater push off force.

The first upper foot member 100 and the second upper foot member 160 of the foot 10, 16 can be separated by a gap 169 that extends between the proximal and distal ends 162, 164 of the second upper foot member 160. The gap 169 is maintained throughout ambulation. This is different than designs of a prosthetic foot in which a gap between two foot members gradually decreases as the prosthetic foot transitions from heel-strike to toe-off and the two foot members gradually make contact when being loaded, thereby acting as a stiffening feature. In the present disclosure, the second upper foot member 160 maintains a maximum second upper foot member lever arm because the contact areas between the second upper foot member 160 and the first upper foot member 100 remains only to be at the adapter 170 and the first spacer 122. In addition to the single first spacer 122 or the upper portion 122A of the two-part first spacer, as shown in FIGS. 1, 8, 16A, and 20, the adapter 170 can also include an adapter spacer 124. Both the first spacer 122 (or the upper and lower portions 122A, 122B) and the adapter spacer 124 can maintain the gap 169 between the second upper foot member 160 and the first upper foot member 100 along the length of the two foot members. When the prosthetic foot 10, 16 is loaded, the first spacer 122 (or the upper and lower portions 122A, 122B) and the adapter spacer 124 can be the only contact points through which the second upper foot member 160 can contact the first upper foot member 100, thereby keeping the lever arm of the second upper foot member 160 long.

The gap 169 can serve several functions. The gap 169 can keep the contact point of the second upper foot member 160 with the remainder of the foot 10, 16 in the distal region more forward at the area where the bolt 111 is located. If the contact point becomes more rearward by reducing the gap 169, the lever arm of the second upper foot member 160 will become shorter and both the ankle motion and push-off power will be reduced. The gap 169 can maintain a more springy flexible connection between the second upper foot member 160 and the first upper foot member 100 to allow the distal end 164 of the second upper foot member 160 to shift and allow for a more controlled motion in a torsional direction (that is, in the coronal plane). During rollover of the forefoot, the contact point on the second upper foot member 160 with the first spacer 122 can shift anteriorly (for example, by about 2 mm to about 5 mm) when the distal end 164 of the second upper foot member 160 moves more posteriorly relative to the first spacer 122. Thus during rollover of the forefoot, the second upper foot member 160 is less stiff than if the distal end of the second upper foot member 160 were to be fastened or bolted to the first upper foot member 100. With a softer second upper foot member 160, during rollover of the forefoot, the foot 10, 16 plantar-flexes more easily, resulting in a smoother rollover and absorbing more impact. During push off, the distal end 164 of the second upper foot member 160 moves more anteriorly back to the original position, thereby moving the contact point more proximally and shortening the lever arm, which results in a stiffer second upper foot member 160.

With continued reference to FIG. 1 and for example, FIG. 16A, the prosthetic foot 10, 16 can include a first heel bumper 130 between the elongate sole member 110 and the first upper foot member 100. The first heel bumper 130 can absorb shock from impact on the foot 10, 16, such as when landing vertically. A lower surface of the first heel bumper 130 can be fixedly coupled to an upper surface of the elongate sole member 110. The first heel bumper 130 is located more rearward than the bolt 111 and extends toward the heel end of the prosthetic foot 10, 16. The first heel bumper 130 can generally be a wedge in the fore-aft direction tapering toward the toe end of the prosthetic foot 10, 16 such that the thickness of the first heel bumper 130 is greater near its posterior end than near its anterior end.

Optionally, as illustrated in FIG. 1 and for example, FIG. 16A, the prosthetic foot 10, 16 can include a foam sheet 120 between the first upper foot member 100 and the first heel bumper 130. The foam sheet 120 can extend from near the distal end 104 of the first upper member 100 along at least a partial length of the first upper member 100. As shown in FIG. 1, the foam sheet 120 can extend all the way to a second spacer 126 (which will be described in greater details below) such that a distal end of the foam sheet 120 can extend adjacent to or contact a proximal end of the second spacer 126. As shown in FIGS. 16A and 17, the foam sheet 120 may extend up to a step on the first heel bumper 130, for example, a first or the most distal step (which will be described in greater details below) on the first heel bumper 130. The distal end of the foam sheet 120 can extend adjacent to or contact an apex 133 of the first or the most distal step on the first heel bumper 130. Instead of the foam sheet 120, as shown in FIGS. 16A and 17, the first or the most distal step of the first heel bumper 130 can be in contact with a bottom surface of the first upper member 100. A gap 125 can be present between the distal ends of the foam sheet 120/the first heel bumper 130 and the proximal end of the second spacer 126. The gap 125 can help the first upper member 100 during extreme toe impact to bend in a smoother way and in a shape that reduces wear. With the gap 125, the foot 16 can dorsiflex under extreme loads (for example, load exceeding about 7,000 N) by the first upper member 160 contacting the elongate sole member 110 and resisting the loads with the generally C shape of the first upper member 100 rather than the bolts 111, which may easily break the foot 16 in a mechanism similar to the use of a bottle opener.

The foam sheet 120 can have one surface facing the first heel bumper 130 and an opposite surface coupled to a posterior and lower surface of the first upper foot member 100. The foam sheet 120 can have a much smaller thickness than the first heel bumper 130. For example, the thickness of the foam sheet 120 can be in the range of a few millimeters. The foam sheet 120 can provide initial damping and over-damping properties, which can prevent underdamping of the first heel bumper 130 and reduce vibration of the foot 10, 16. The foam sheet 120 and the first heel bumper 130 can work against each other to reduce or remove noise and improve mating of parts of the prosthetic foot 10, 16 (for example, by allowing greater tolerance of the thickness of the first heel bumper 130 while still minimizing any air gap between the first heel bumper 130 and the first upper foot member 100). For example, noise can be reduced or minimized when sand or small particles get between the first upper foot member 100 and the elongate sole member 110. The foam sheet 120 can also reduce flapping noises when the first heel bumper 130 collides with the more rigid parts, such as the first upper foot member 100 during toe-off. The foam sheet 120 can further reduce abrasion between the first upper foot member 100 and the first heel bumper 130. As will be described in greater detail below, the first heel bumper 130 can have a stepped design on the surface facing the first upper foot member 100. The foam sheet 120 can provide a smoother impact when the steps on the first heel bumper 130 hit the first upper foot member 100 during ambulation.

Additionally or alternatively, at least a portion of the first heel bumper 130 can be pre-compressed to minimize and/or prevent an air gap between parts of the foot 10, 16, which can reduce or minimize exposure to small particles or debris, water etc. The pre-compression of the first heel bumper 130 can further reduce noise, for example, when parts of the prosthetic foot 10, 16 slap together. The pre-compressed first heel bumper 130 is also stiffer than an unloaded heel bumper, and therefore increases the stiffness of the foot 10, 16 and the number of working points of the first heel bumper 130 against the first upper foot member 100. The pre-compression also increases the dynamics of the first heel bumper 130 during ambulation, similar to the working principle of the pre-compressed second upper foot member 160 described above.

The stepped design of the heel bumper 130 are illustrated in FIGS. 9A-9B and 18E-18F. The illustrated examples show a 3-step wedge design. However, the number of steps is not limiting and can be varied. A first stepped section 132 is closer to the anterior or distal end of the first heel bumper 130, which is closer to the toe end of the prosthetic foot 10, 16. A second stepped section 134 is immediately rearward of the first stepped section 132. A third stepped section 136 is immediately rearward of the second stepped section 134 and terminates at the posterior end of the first heel bumper 130. In each section, a thickness of the first heel bumper 130 increases gradually from an anterior end to a posterior end. The posterior ends 133, 135 of the first and second stepped sections 132, 134 can each be higher than the anterior end of the immediately adjacent section, resulting in a step or ridge at the posterior end of each section. The posterior ends 133, 135 of the first stepped section 132 and the second stepped section 134 can each be shorter than the posterior end of the immediately adjacent section such that the first heel bumper 130 has an overall wedge shape.

As shown in FIGS. 9A-9B and 18E-18F, at least the first stepped section 132 can include a plurality of grooves 131. The other sections can also include one or more grooves. The grooves 131 can allow air to circulate through the grooves 131 and any water in the first heel bumper 130 to dry off. The grooves 131 can also provide a route for any dirt or debris to leave the first heel bumper 130 and/or to prevent noise.

During ambulation, the posterior end 133 of the first stepped section 132 can bend the first upper foot member 100 into plantarflexion. In other words, the first stepped section 132 can initiate plantarflexion during ambulation. In some examples, the first stepped section 132 can absorb up to about 80% of an amputee's body weight. In the foot 10 shown in FIG. 1, the first stepped section 132 can be pre-compressed by the foam sheet 120. In the foot 16 shown in FIG. 16A, the first stepped section 132 can be pre-compressed by the first upper member 100. The pre-compressed first stepped section 132 can minimize air gap between the heel bumper 130 and the foam sheet 120 (such as shown in FIG. 1) and/or the first upper foot member 100 (such as shown in FIG. 17). The amount of pre-compression can be set by a second spacer 126 (described in more detail below) depending on the thickness of the second spacer 126. For example, the pre-compression can be about 20% to about 40% of the thickness of the first stepped section 132.

As the foot 10, 16 plantarflexes more, the second stepped section 134 can contact the foam sheet 120 and/or the first upper foot member 100 to catch the foot 10, 16 at a greater dynamic load and reduce further plantarflexion. At the greater load, the first heel bumper 130 deforms more to provide damping. In some examples, the second stepped section 134 can absorb up to about 120% of an amputee's body weight.

The third stepped section 136 can prevent overload of the foot 10, 16 during extreme heel strikes. The third stepped section 136 can contact the foam sheet 120 and/or the first upper foot member 100 when the foot 10, 16 plantarflexes to more than 15 degree. In such situations, the third stepped section 136 can be deformed (that is, compressed) to prevent further plantarflexion of the foot 10, 16, which can prevent severe overload of the foot 10, 16.

Figure 10:
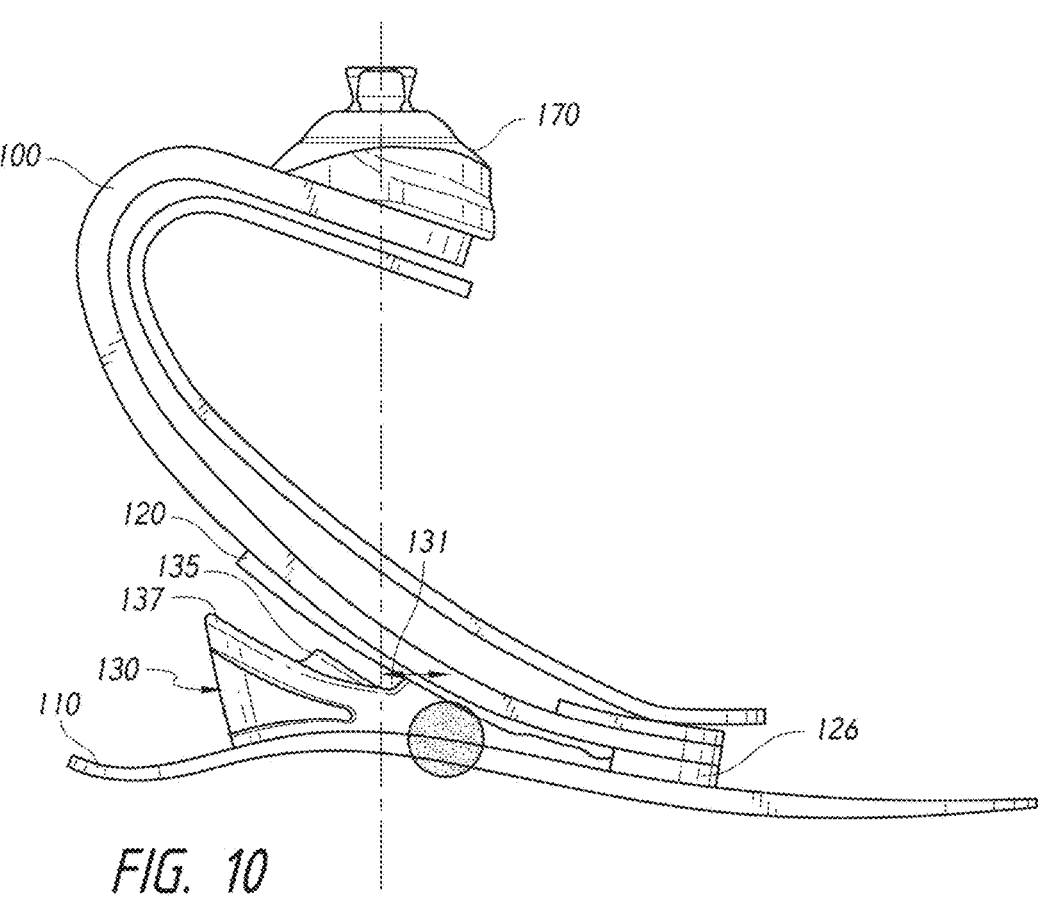
FIG. 10 illustrates dimensions of the stepped heel bumper relative to an adapter of the prosthetic foot of FIG. 1.

Lengths of the stepped sections 132, 134, 136 can be determined based on position of the adapter 170. As shown in FIG. 10 with the prosthetic foot 10 as an example, the steps of the first heel bumper 130 can be aligned with various locations relative to the position of the adapter 170 in order to initiate plantarflexion (that is, bending the first upper foot member 100 around the step or ridge at the posterior end 133 of the first stepped section 132) and to reduce the amount of deformation of the foot 10, 16 by reducing the amount of deforming of the first heel bumper 130. The position of the adapter 170 can define a theoretical load line (the "⅓ line") at ⅓ of a length of the prosthetic foot 10, 16 from the heel end. The posterior end 133 of the first stepped section 132 can be anterior (that is, in the direction of the toe end) to the ⅓ line by a distance that is of about 2% to about 10%, or about 6%, of the total foot length. The posterior end 135 of the second stepped section 134 can be at least behind or posterior to the ⅓ line in order to prevent further bending of the first upper foot member 100. For example, the posterior end 135 of the second stepped section 134 can be posterior to the ⅓ line (in direction towards the heel end) by greater than about 2% of the total foot length. The posterior end 137 of the third stepped section 136 can be behind the second stepped section 134 in order to function as an end stop and prevent any further plantarflexion as described above.

Figure 19A:
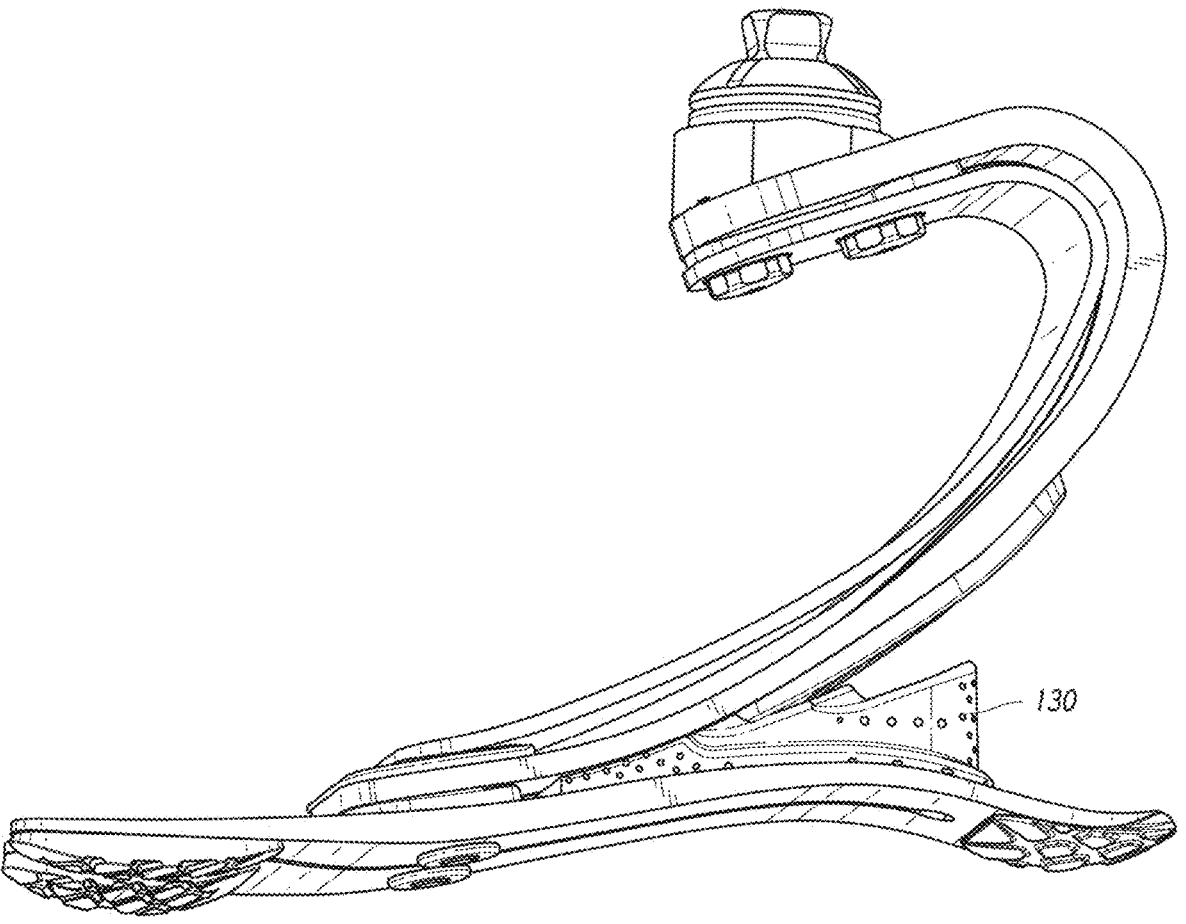
FIG. 19A illustrates a perspective view of a prosthetic foot disclosed herein with a first heel bumper having a three-dimensional (3D) printed lattice structure.
Figure 19B:
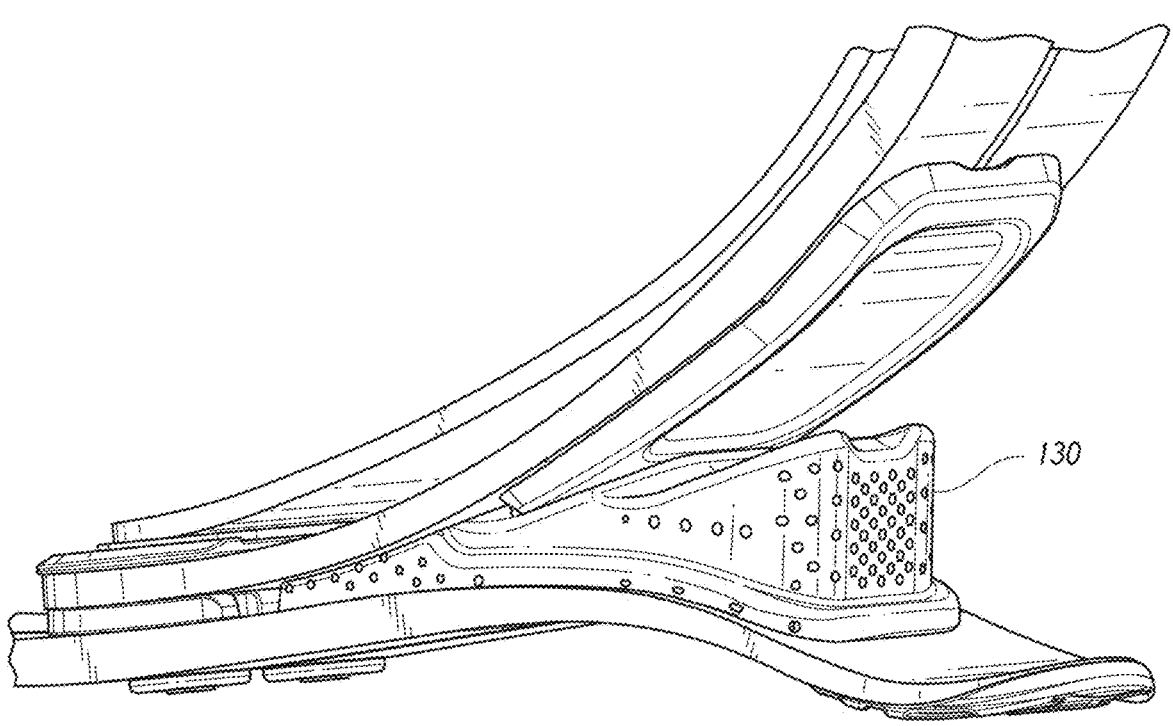
FIG. 19B illustrates a partial view of a prosthetic foot disclosed herein with the first heel bumper having the 3D printed lattice structure.

The first heel bumper 130 of the foot 10, 16 can be made of various suitable materials. For example, the first heel bumper 130 can be made of a foam material. As another example, the first heel bumper 130 can be made of a 3D-printed soft material, for example, but not limited to, a polyurethane (PU) foam, rubber, eTPU, thermoplastic elastomer (TPE), Elastomeric polyurethane (EPU) or any other materials with a low compression set, high rebound and a shore hardness of about 30 to 70 Shore A. As shown in FIGS. 19A-19B, the 3D-printed first heel bumper 130 may include a lattice structure. The lattice structure may be functional and may be located internally in the first heel bumper 130. The functional lattice structure may vary with different stiffness requirements, which may correlate to a predetermined user weight. The lattice structure may not be apparent on an outer surface of the first heel bumper 130. Instead, the outer surface of the first heel bumper 130 in FIGS. 19A-19B can have an even appearance. The smooth outer surface can allow for cleaning of the support material used during the manufacturing process. During the manufacturing process, a visual outer lattice and technical inner lattice structure can be placed on the outside of the first heel bumper. By 3D printing the lattice structure, which may not be uniform throughout the first heel bumper 130, the first heel bumper 130 can have a hybrid stiffness. For example, the 3D printed first heel bumper 130 as shown in FIGS. 19A-19B can have a very stiff anterior section, a semi-stiff intermediate section, and a soft rear section to create a progressive overload protection. Compared to the foam heel bumper, the 3D printed heel bumper can have both a defined stiffness within the different zones posterior to the heel bumper to provide at each section an optimal amount of cushioning and springiness. Furthermore the 3D printed bumper can change its stiffness from medial to lateral side and/or can have a stiff middle section and softer/stiffer outer sides. Compared to the foam heel bumper, the 3D printed heel bumper can provide higher plantarflexion (heel strike) as it is stiffer. As a result, the foot may feel softer as the foot can plantarflexion to a greater extent.

Figure 11:
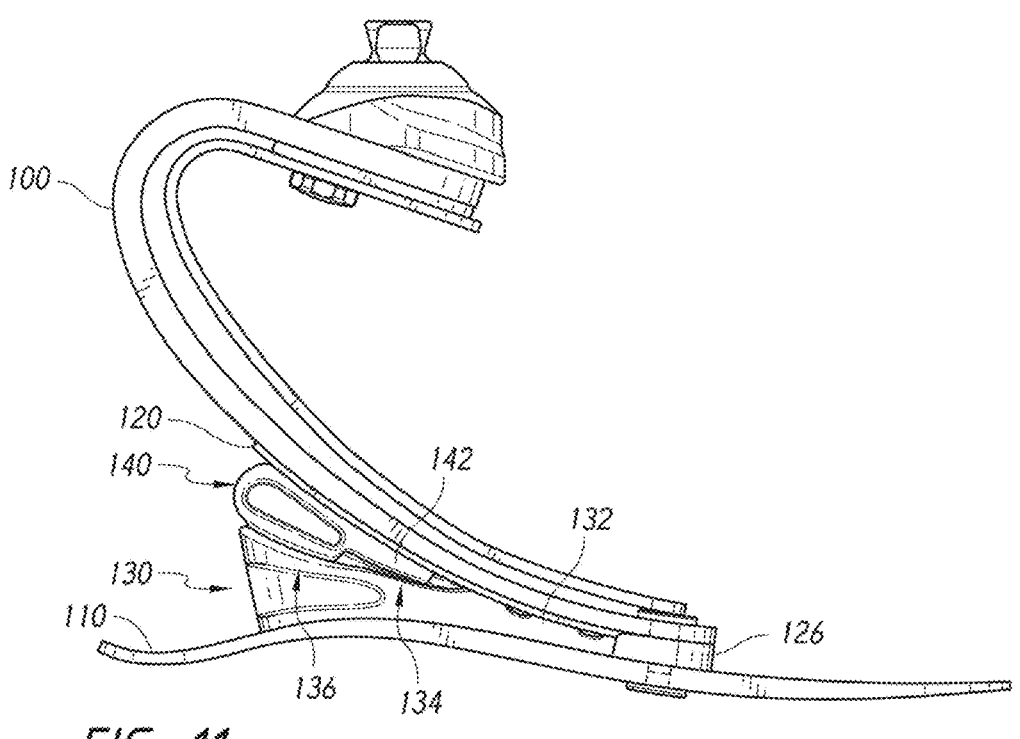
FIG. 11 illustrates a variation of the prosthetic foot of FIG. 1 with a second heel bumper.

Optionally, one or more additional stiffening bumpers can be added to the prosthetic foot 10, 16. The additional stiffening bumper(s) can be removable. As shown in FIG. 11, a second heel bumper 140 can be inserted between the foam sheet 120 and the first heel bumper 130 of the foot 10. The second heel bumper 140 can have a first portion 142 that fills a first gap between the foam sheet 120 and the second stepped section 134. The first portion 142 can reduce further plantarflexion of the foot 10. Loading of the foot 10 can deform the first portion 142 of the second heel bumper 140 and the foot 10 can start earlier rolling of the forefoot instead of resulting in more motion in the ankle joint. The second heel bumper 140 that may be added to the prosthetic foot 10 can have a second portion 144 that fills in a second gap between the foam sheet 120 and the third stepped section 136. The second portion 144 can reduce further plantarflexion of the foot 10 to a greater extent than the first portion 142, thereby further stiffening the heel portion of the foot 10. The second heel bumper 140 can be added to the foot for higher impact sports activities, for example, weightlifting. Alternatively, the second heel bumper may include only the first portion 142 without having the second portion 144 that fills in the gap between the foam sheet 120 and the third stepped section 136 of the heel bumper 130.

Figure 18C:
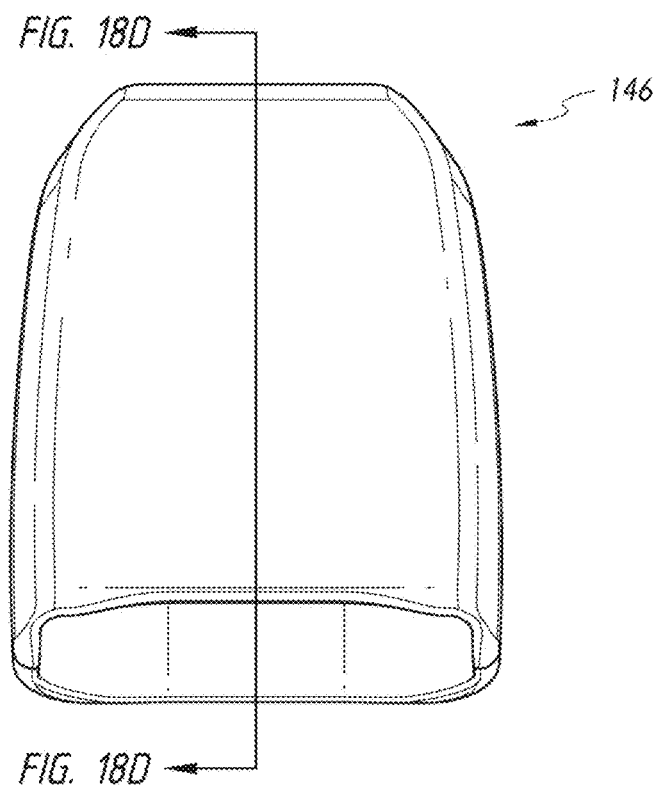
FIG. 18C illustrates a front view of the second heel bumper shown in FIG. 18A.
Figure 18D:
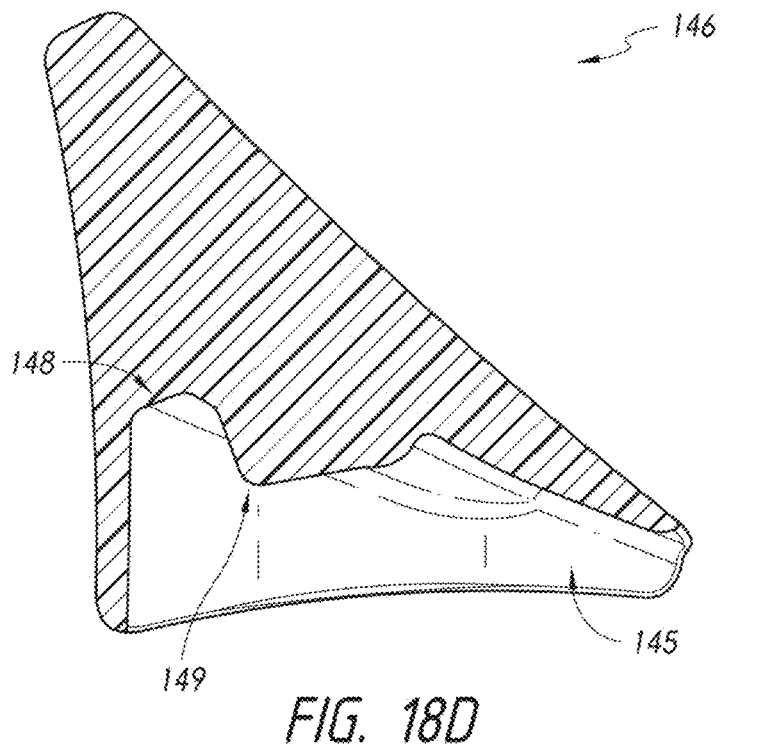
FIG. 18D illustrates a cross-sectional view of FIG. 18C along the axis D-D.
Figure 18E:
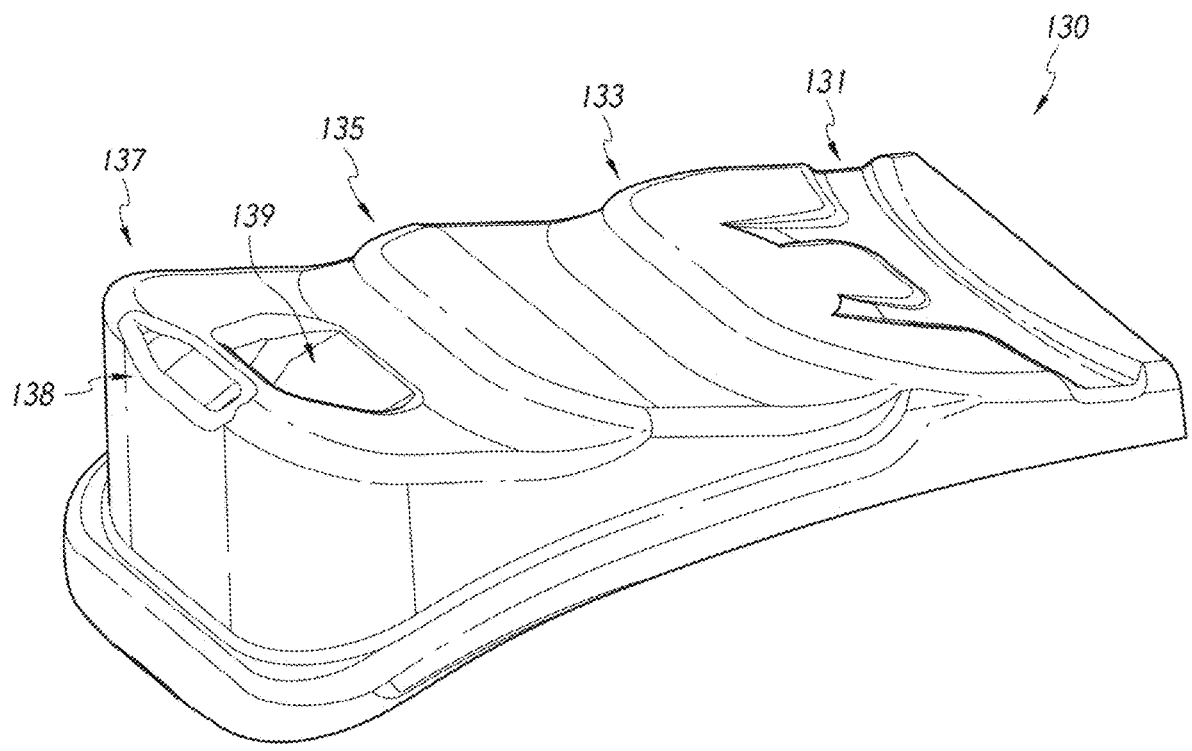
FIG. 18E illustrates a perspective view of a first heel bumper shown in FIG. 18A.
Figure 18F:
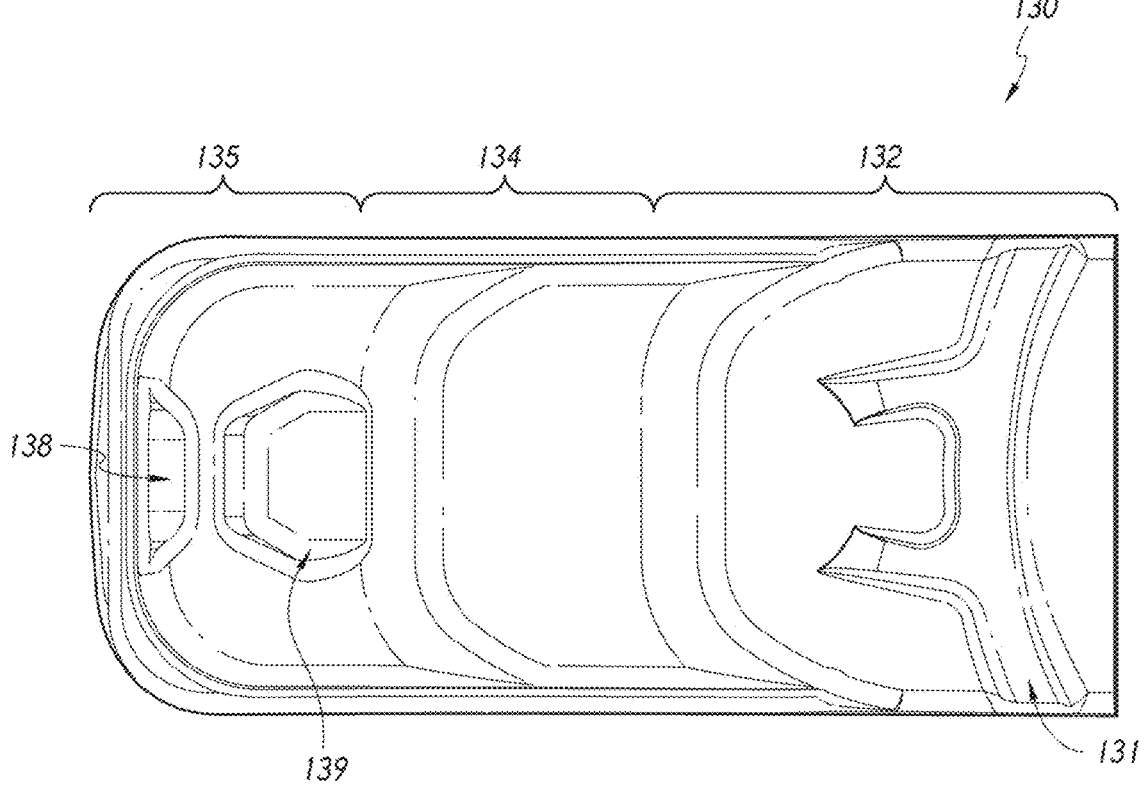
FIG. 18F illustrates a top view of the first heel bumper shown in FIG. 18A.
Figure 18G:
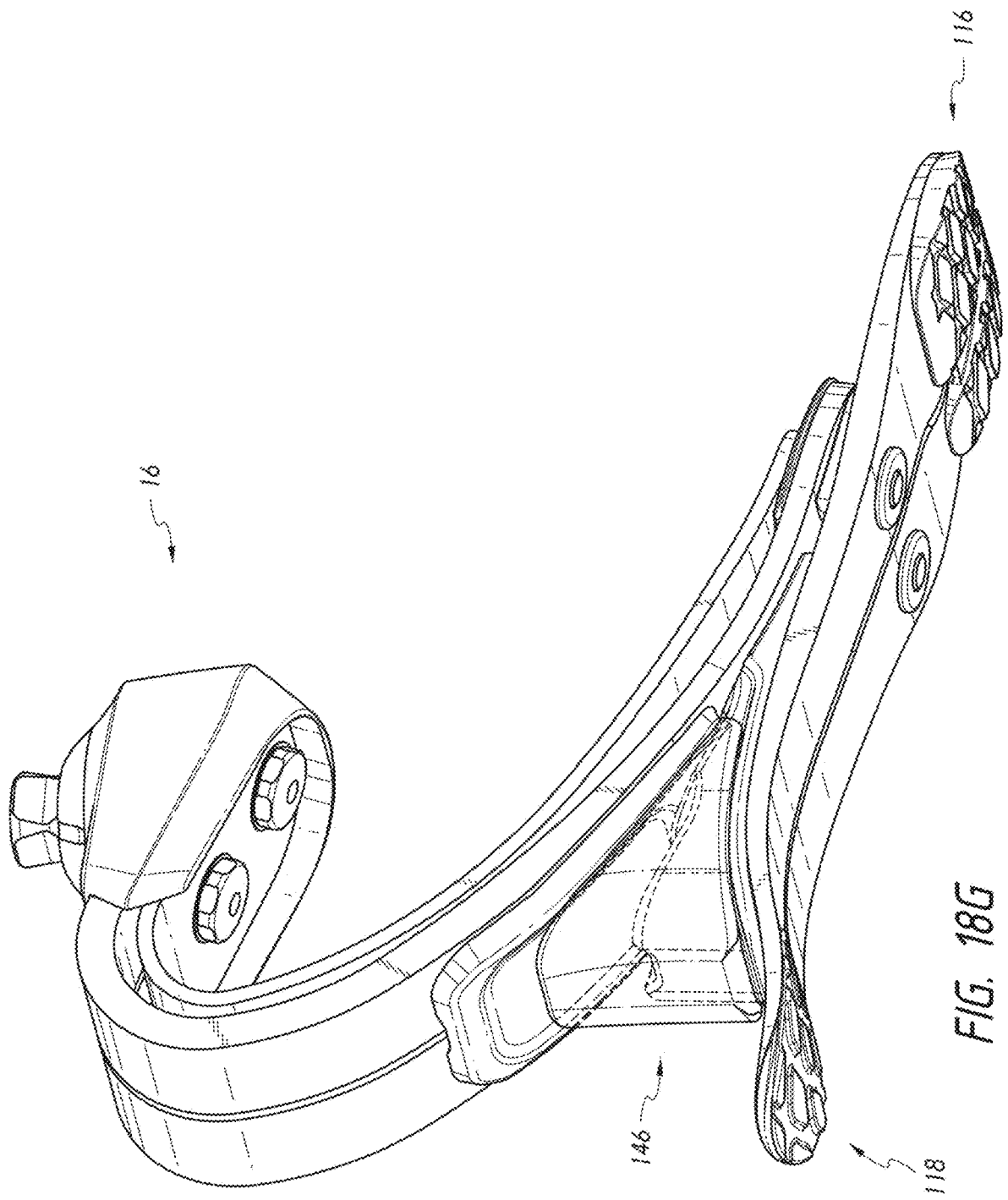
FIG. 18G illustrates a perspective view of the foot of FIG. 16A with the second heel bumper shown in FIG. 18A.
Figure 18H:
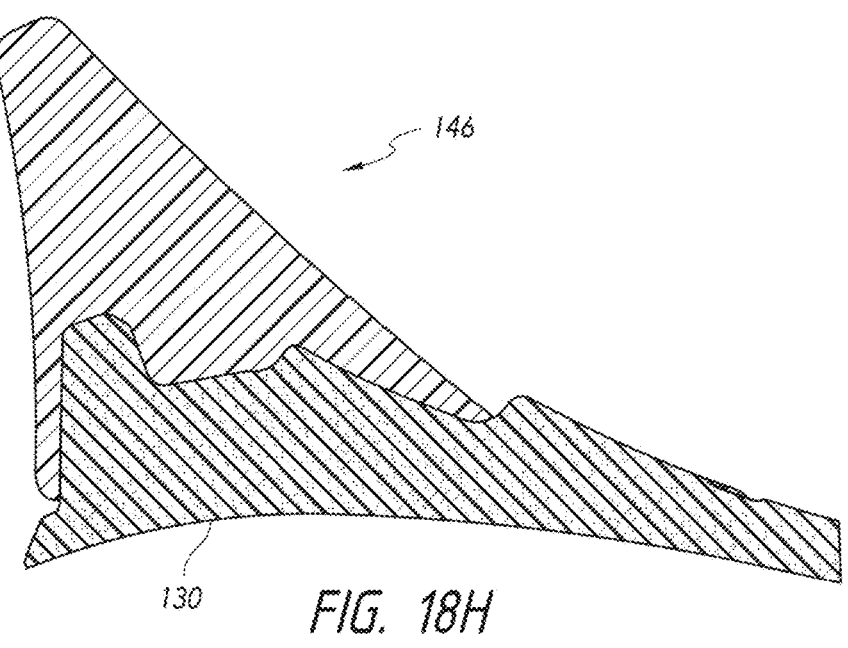
FIG. 18H illustrates a cross-sectional view of the first heel bumper and the second feel bumper shown in FIG. 18A.

FIGS. 18A-18H illustrate the prosthetic foot 16 with a removably coupled second heel bumper 146. As shown in FIG. 18B, an outer surface of the second heel bumper 146 can have a generally wedge shape, with a greater height on a posterior or rear end compared to an anterior or front end. The outer surface of the second heel bumper 146 can cover (for example, completely cover) a portion of the first heel bumper 130 on the lateral sides. The second heel bumper 146 can include an internal cavity 145 to receive the portion of the first heel bumper 130. The internal cavity 145 can include one or more guide features to guide the second heel bumper 146 onto the first heel bumper 130. As shown in FIGS. 18B-18D, the internal cavity 145 of the second heel bumper 146 can include generally a hump 149. As shown in FIGS. 18E and 18H, the hump 149 can correspond to a chamfered indent 139 formed in the third stepped section 136 of the first heel bumper 130, proximal or posterior to the posterior end 135 of the second stepped section 134. In some examples, the internal cavity 145 of the second heel bumper 146 can include a protrusion 148 corresponding to an indent 138 at or near the posterior end 137 of the third stepped section 136 of the first heel bumper 130. The mating between the hump 149 and the chamfered indent 139, and/or the mating between the protrusion 148 and the indent 138 can facilitate insertion of the second heel bumper 140 by guiding the second heel bumper 140 into its seat between the foam sheet 120 and the first heel bumper 130.

The second heel bumper 146 can stiffen the heel section of the foot 16. The second heel bumper 146 can do so by, for example, reducing the rotation (such as plantarflexion) of the foot 16 and acting as a vertical shock adapter, such as a stiffening vertical shock adapter of the foot 16. With the second heel bumper 146 inserted as shown in, for example, FIGS. 18A and 18G-18H, the first upper foot member 100 can impart a force on or engage the entire length of the first heel bumper 130. The use of the second heel bumper 146 can alter the characteristics of the foot 16 in ways that may be preferred or more helpful to users that need to load the heel region of the prosthetic foot 16 more and want reduced motion in the heel region, or users that engage in, for example, sport activities such as weightlifting, running, and the like, and need more support (including, for example, less motion in the heel section) from the foot. Compared to a foot without the second heel bumper 140, a foot with the first and second heel bumpers 130, 140 (for example, when both are 3D printed) can have a stiffer heel. The foot with the second heel bumper 140 can stop plantarflexion earlier and roll over to midstance sooner than a version without the second heel bumper 140.

The second heel bumper 146 can also help adjust a heel height of the foot 16 by bringing the foot 16 (for example, as shown in FIG. 18A) into a more dorsiflexed position than if the second heel bumper 146 is not inserted (for example, as shown in FIG. 16A).

To insert the second heel bumper 146, a user can open a rear section of the foot 16, for example, by leaning over the toe region and pushing the second heel bumper 146 from behind as far into the foot 16 until the guiding features disclosed herein snap into the respective indent or recess. Optionally, the second heel bumper 146 can be kept in place by fastening mechanisms or adhesive. The second heel bumper 146 may not need any fastening mechanisms and can be inserted and removed when desired by the user. The flexibility of using or not using the second heel bumper 146 can allow the user to alter the roll-over characteristics of the prosthetic foot 16 depending on the physical activity, for example, by inserting the second heel bumper 146 for engaging in sports activities and removing the second heel bumper 146 for walking.

The second heel bumper 140, 146 of the foot 10, 16 may have a different stiffness than the stiffness of the first heel bumper 130. For example, the second heel bumper 140, 146 may have a greater stiffness than the first heel bumper 130 and may be referred to as a stiffening bumper. Alternatively, second heel bumper 140, 146 can be semi-rigid. For example, the second heel bumper 140, 146 can have a stiffness similar or lower than the stiffness of the first heel bumper 130. A semi-rigid second heel bumper 140, 146 can induce more damping in the foot 10, 16. Furthermore, as described above, the second heel bumper 140, 146 can decrease the ankle range of motion during heel strike, thereby changing the rollover characteristics. With the second heel bumper 140, 146, there can be more rolling over the elongate sole member 110 like rolling over a wheel than bending a system of springy foot members made of carbon fiber. The second heel bumper 140, 146 may be made of foam, or alternatively of a 3D-printed lattice structure similar to the first heel bumper 130 as shown in FIGS. 19A-19B. The second heel bumper 140, 146 may be made with a similar manufacturing process as the first heel bumper 130, including for example, providing a hybrid stiffness in different sections of the second heel bumper 140, 146. For example, the second heel bumper 140 can be 3D printed to provide multiple functions, such as multiple density stiffness (for example, stiff middle part and softer and more flexible sides).

Figure 12A:
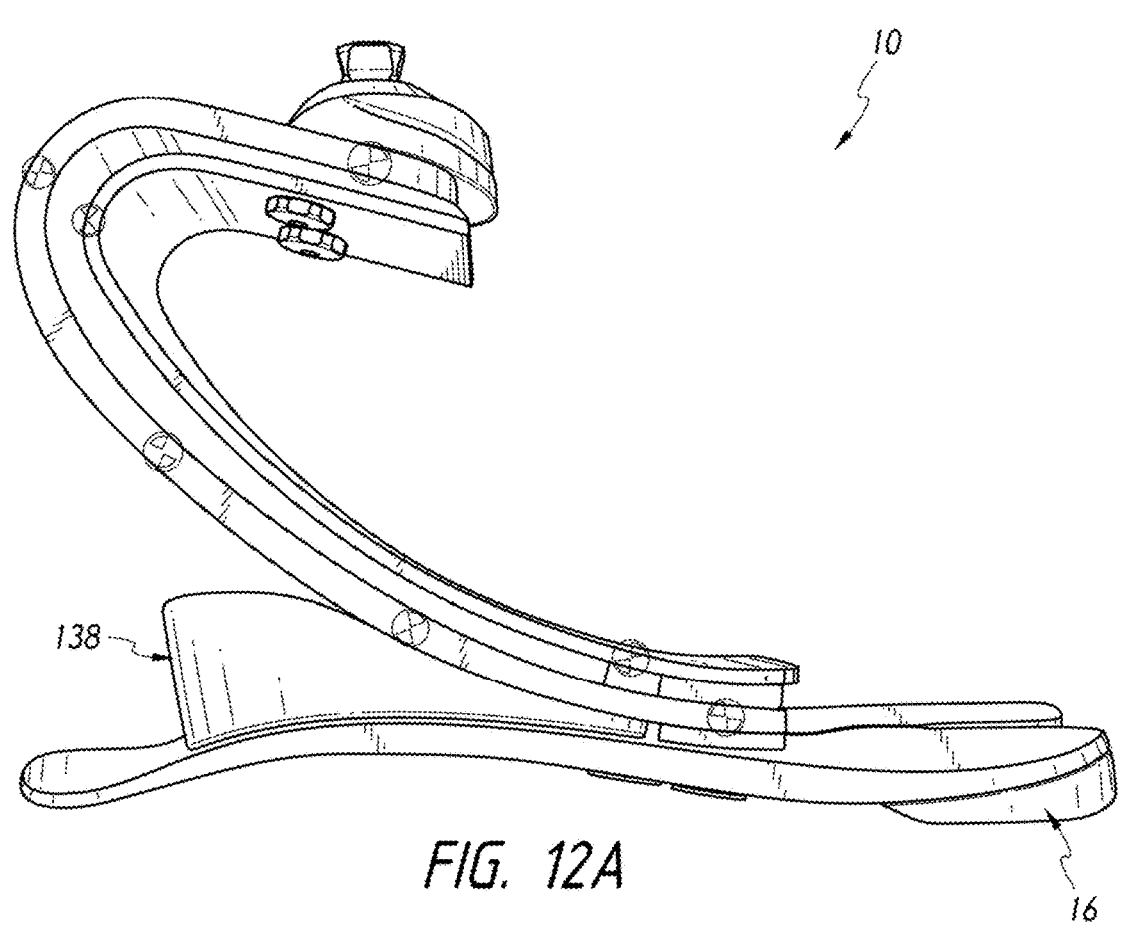
FIG. 12A illustrates a variation of the prosthetic foot of FIG. 1 with a smooth heel bumper.
Figure 12B:
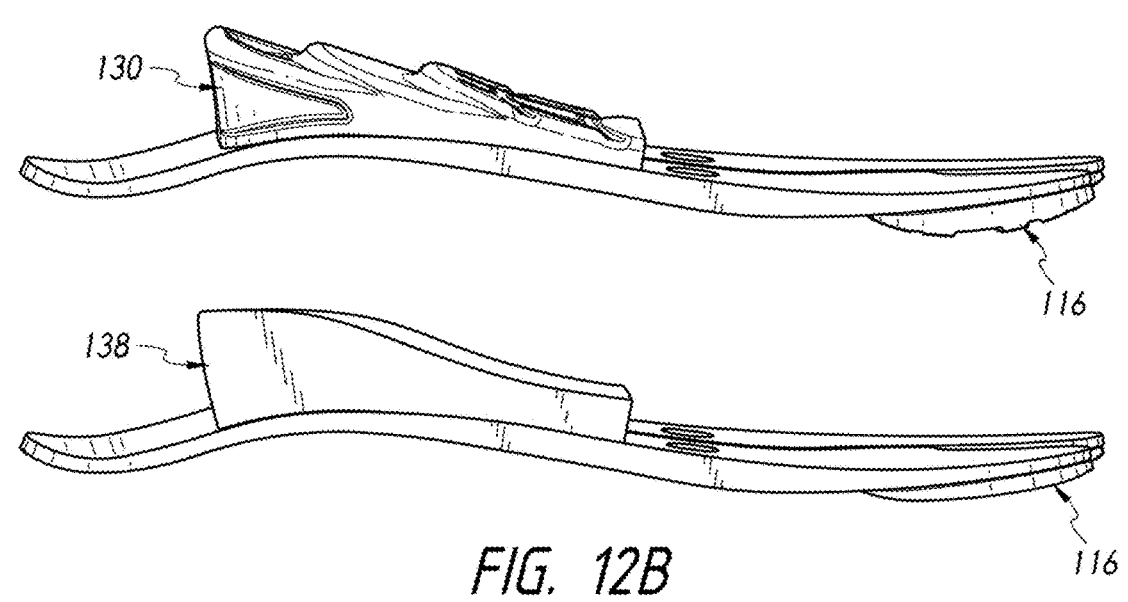
FIG. 12B illustrates a side-by-side comparison of the stepped heel bumper and the smooth heel bumper.

One alternative approach to the stepped design of the heel bumper 130 is to replace the steps with a smooth transition line following the steps, such as shown in FIGS. 12A and 12B. The foot 10 in FIG. 12A can have any of the features of the foot in FIG. 1, except that the stepped heel bumper 130 is replaced by a smooth-lined heel bumper 138. The prosthetic foot 16 disclosed herein may alternatively include a smooth-lined heel bumper 138. The smooth-lined heel bumper 138 can cause the loading of the foot to be more evenly spread out when loading the heel. However, the heel stiffness with the smooth-lined heel bumper 138 may be more determined by the stiffness of the smooth-lined heel bumper 138 and plantarflexion motion may be initiated later. That is, the heel will be deformed first before the foot is bent into plantarflexion when the smooth-lined heel bumper 138 is included instead of the stepped heel bumper 130. Although FIGS. 12A-12B show a toe pad 116 below the elongate sole member 110 at the toe section, the pad 116 is optional and is not required for the heel bumpers disclosed herein to function as described. The prosthetic foot 10 of FIG. 1 may also optionally include a toe pad 116 and/or a heel pad 118.

As shown in, for example, FIGS. 1, 13A, 16A, and 17, the prosthetic foot 10, 16 can include a second spacer 126. The second spacer 126 can be between the first upper foot member 100 and the elongate sole member 110 to create a distance between the first upper foot member 100 and the elongate sole member 110. The second spacer 126 can be located near the bolt 111, at or near the distal end 104 of the first upper foot member 100. As described above, the first heel bumper 130 can extend up to the second spacer 126 in the prosthetic foot 10. In the prosthetic foot 16, the first heel bumper 130 may not extend all the way to the second spacer 126. In the foot 16, the gap 125 can be formed between a distal end of the first heel bumper 130 and a proximal end of the second spacer 126.

Figure 13A:
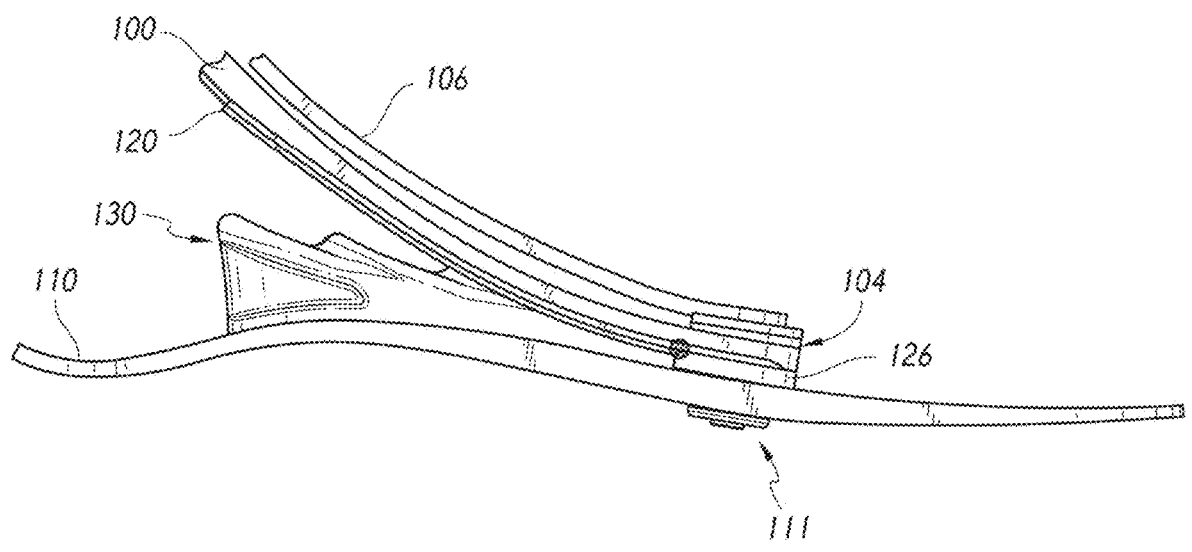
FIG. 13A illustrates a pivot point of the first upper member of the prosthetic foot of FIG. 1.
Figure 13B:
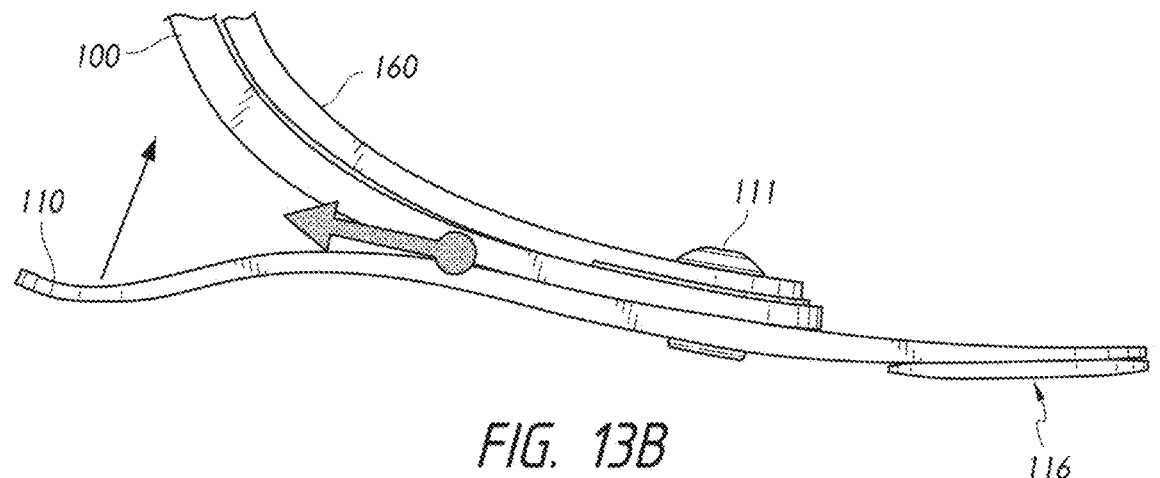
FIG. 13B illustrates a pivot point of a first upper member of a prosthetic foot without a spacer between the first upper member and the elongate sole member.

The second spacer 126 can allow the first upper foot member 100 to pivot about a point more toward the toe end, increasing the lever arm of the first upper foot member 100. Such a pivot point is shown as a yellow dot in FIG. 13A, which is illustrated with the prosthetic foot 10 as an example. In contrast, as shown in FIG. 13B, if the first upper foot member 100 is directly connected to the elongate sole member 110 without the second spacer 126, the pivot point (illustrated as a yellow dot) around which the first upper foot member 100 bends would tend to be more backwards. Moreover, the pivot point would move even more rearward (as indicated by the arrow to the left of the yellow dot in FIG. 13B) during plantarflexion when a distal section of the first upper foot member 100 contacts the elongate sole member 110, which can further stiffen up the foot 10, 16 during heel strike.

Additionally, in the foot 10, the second spacer 126 compresses the foam sheet 120 and/or the first stepped section 132 of the heel bumper 130 between the elongate sole member 110 and the first upper foot member 100. The pre-compression by the second spacer 126 can create a higher stiffness in the first stepped section 132 of the heel bumper 130 to bend the first upper foot member 100, but allows the heel bumper 130 to remain softer in the second stepped section 134 and the third stepped section 136 to provide a smoother contact collision and to only as an end stop when the maximum desired amount of plantarflexion is achieved.

Figure 14:
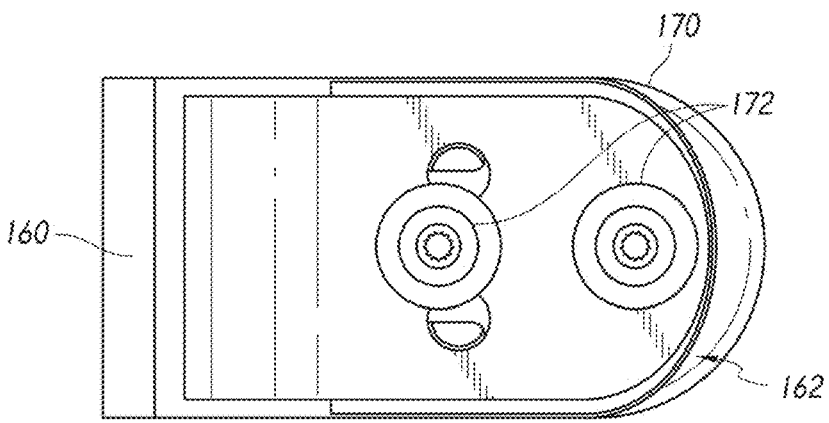
FIG. 14 illustrates a bottom view of an example pyramid of the prosthetic foot of FIG. 1.
Figure 15A:
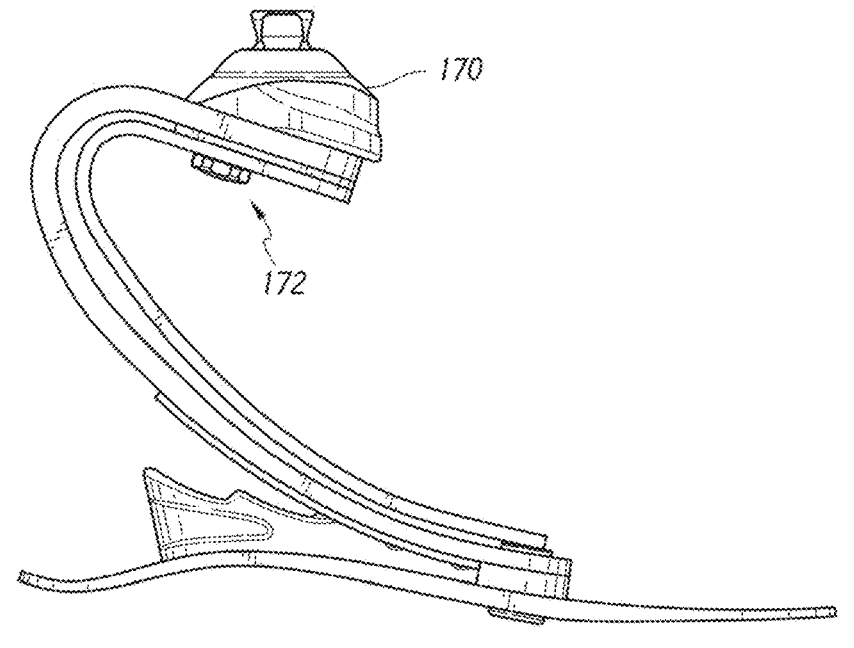
FIG. 15A illustrates a variation of the prosthetic foot of FIG. 1 with an alternative pyramid mounting mechanism than as shown in FIG. 14.
Figure 15B:
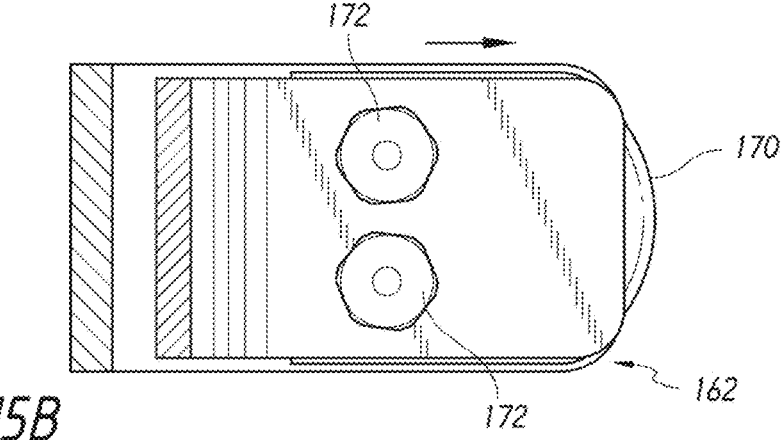
FIG. 15B illustrates a bottom view of the pyramid shown in FIG. 15A and other possible variations.
Figure 20:
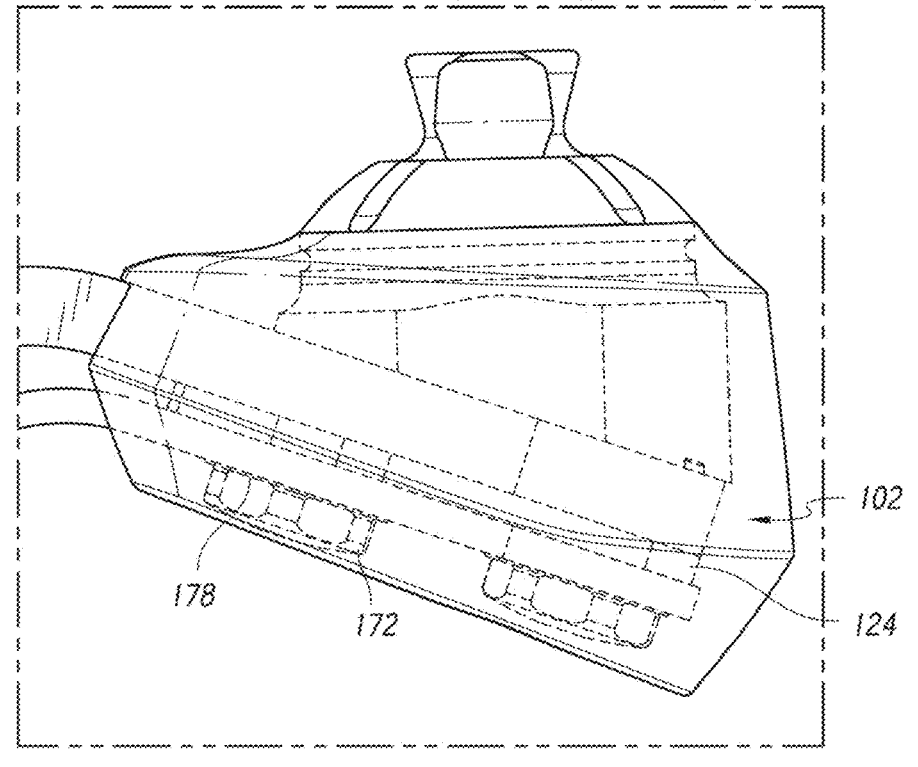
FIG. 20 illustrates a second detailed view of the foot shown in FIG. 16A.

FIGS. 14 and 15A-15B illustrates different ways to attach the adapter 170 to the first upper foot member 100 and second upper foot member 160 using one or more adapter bolts 172. The size of the adapter bolts 172 can include, for example, 2×M10 (such as shown in FIG. 1) or 2×M12 (such as shown in FIGS. 16A and 20). As more clearly shown in FIG. 20, a washer 178 may be used with the bolt 172. FIG. 1, FIG. 14, and FIG. 16A illustrate two adapter bolts 172 aligned in the fore-aft direction. The alignment can allow for more foot member material around the adapter bolts 172 on each lateral side of the first upper foot member 100 and the second upper foot member 160. FIG. 15A illustrates a prosthetic foot 10 having any of the features of FIG. 1, FIG. 16A, or FIG. 18A, except that the adapter bolts 172 are aligned in a mediolateral direction. Alternatively, the location of the adapter bolts 172 aligned in the mediolateral direction may be moved more anteriorly, as shown by the arrow in FIG. 15B to be closer the proximal end 162 of the second upper foot member 160. The more anterior locations of the adapter bolts 172 can allow for a longer active lever arm of the first upper foot member 100 and the second upper foot member 160.

The construct of the pyramid adapter 170 may vary. In FIG. 1, the adapter 170 may include a metallic (for example, stainless steel or the like) pyramid portion 171 coupled to a plastic adapter portion 173. In FIGS. 16A and 20, the adapter 170 may include a metallic (for example, stainless steel or the like) pyramid insert 175 with an over-molded plastic cover 177.

Figure 21A:
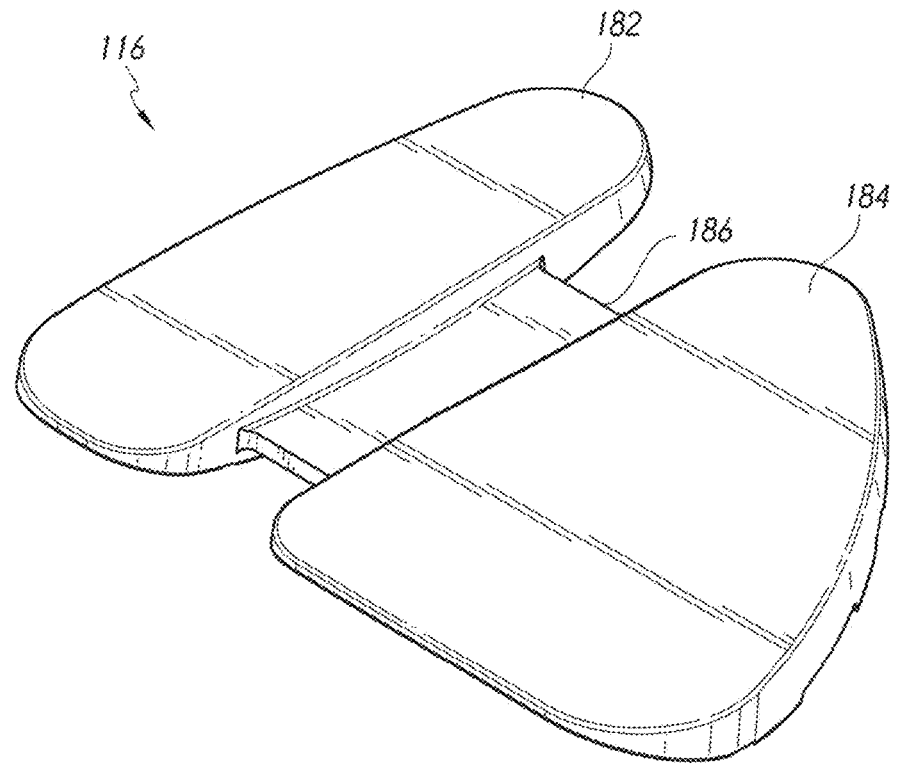
FIG. 21A illustrates a top perspective view of a toe pad as shown in FIG. 16A.
Figure 21B:
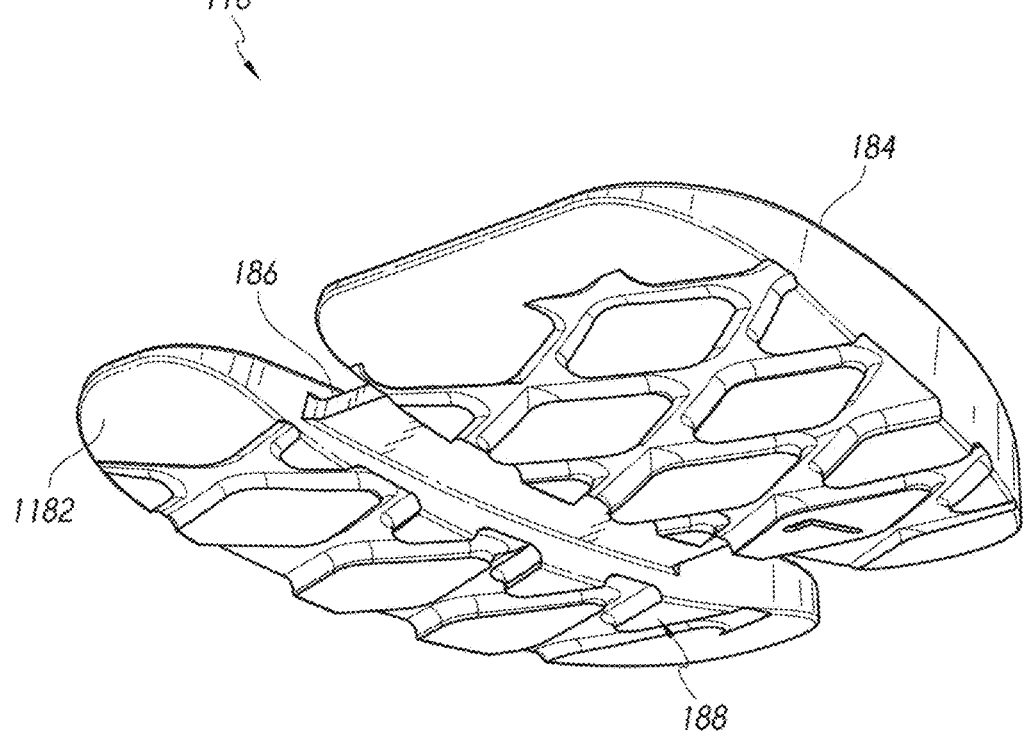
FIG. 21B illustrates a bottom perspective view of a toe pad as shown in FIG. 16A.

Similar to the prosthetic foot 10 (see FIGS. 12A-12B), as shown in, for example, FIGS. 16A and 18A, the prosthetic foot 16 can include a toe pad 116. The toe pad 116 can be under the toe region of the elongate sole member 110. The toe pad 116 can be coupled to an underside of the elongate sole member 110 using any suitable mechanisms, such as adhesives, magnets, screws, and the like. As shown in FIGS. 21A and 21B, the toe pad 116 can include a lateral portion 184 and a medial portion 182. A shape and size of the lateral portion 184 and/or medial portion 182 can conform substantially to shapes and sizes of the medial and lateral portions of the elongate sole member 110 at the toe region. The lateral portion 184 and the medial portion 182 may not have a uniform thickness. Along a longitudinal axis of the foot 10, 16, a bottom surface of the lateral portion 184 and the medical portion 182 may be curved with the thickness gradually increasing from the anterior and posterior ends of the toe pad 116 toward a center region of the toe pad 116.

The toe pad 116 can include a bridge 186 between the lateral portion 184 and the medial portion 182. As shown in FIGS. 21A and 21B, the bridge 186 can be thinner than a thickness of the lateral portion 184 and/or medial portion 182. The bridge 186 can be located across a U-shaped gap 117 of the elongate sole member 110. The bridge 186 may not contact a support surface (for example, the ground) when the foot is resting on the support surface. Alternatively, the toe pad can include separate lateral and medial portions, omitting the bridge.

Figure 22A:
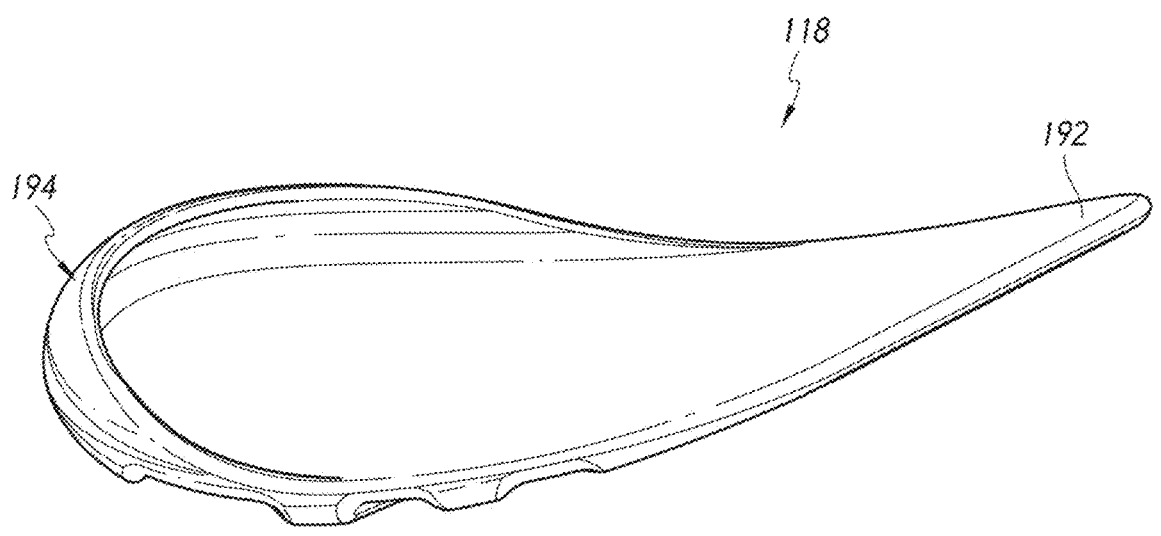
FIG. 22A illustrates a top perspective view of a heel pad as shown in FIG. 16A.
Figure 22B:
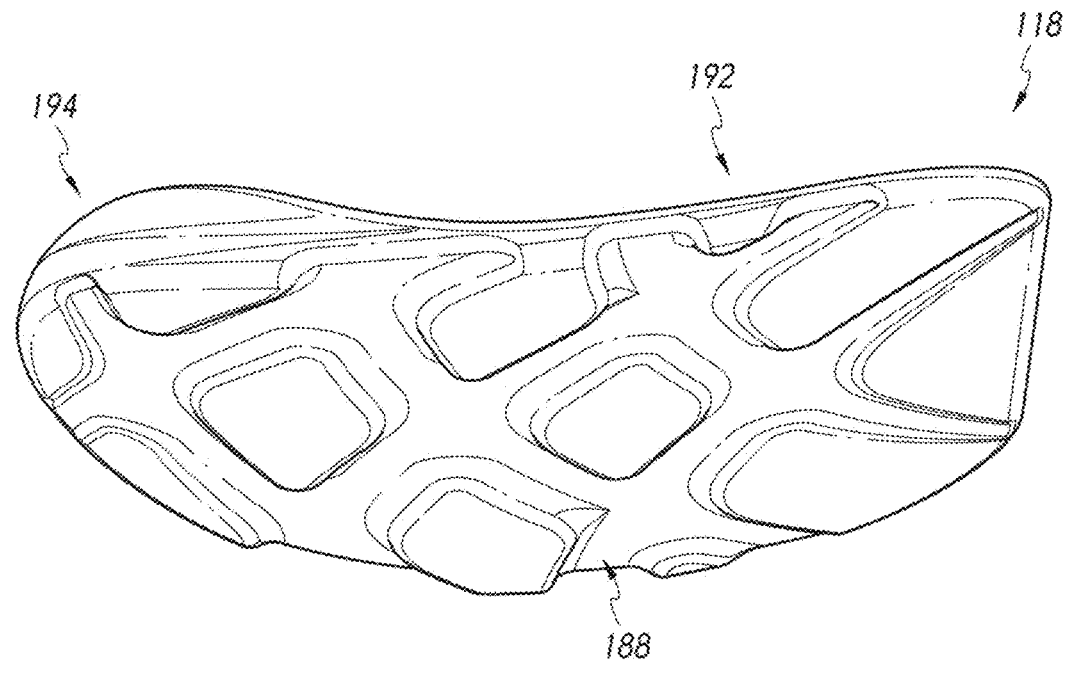
FIG. 22B illustrates a bottom perspective view of a heel pad as shown in FIG. 16A.

As shown in, for example, FIGS. 16A and 18A, the prosthetic foot 16 can include a heel pad 118. The heel pad 118 can be generally under the heel region of the elongate sole member 110. As shown in FIGS. 22A and 22B, the heel pad 118 can include a pad portion 192 and a lip portion 194. A shape and size of the pad portion 192 can conform substantially to shapes and sizes of the elongate sole member 110 at the heel region. The lip portion 192 can extend around a heel end of elongate sole member 110 along its thickness. A height of the lip portion 192 can be shorter or generally the same as the thickness of the elongate sole member 110. At least the pad portion 192 can be coupled to an underside of the elongate sole member 110 using any suitable mechanisms, such as adhesives, magnets, screws, and the like. The heel pad 118 may or may not have a uniform thickness. For example, the pad portion 192 may have a greater thickness toward a posterior or heel end of the pad portion 192 than a more anterior end of the pad portion 192. A curvature of the heel pad 118 can generally follow a curvature of the heel region of the elongate sole member 110.

The prosthetic foot 10 may include the toe pad 116 and/or the heel pad 118. The toe pad 116 and/or the heel pad 118 can improve grip of the prosthetic 10, 16 and/or provide protection of the elongate sole member 110 against wear and tear. As shown in FIGS. 21A-21B and 22A-22B, the bottom surfaces of the toe pad 116 and the heel pad 118 can include one or more grooves 188 or patterns to improve grip. Additionally or alternatively, the bottom surfaces of the toe pad 116 and the heel pad 118 can include textured surfaces, which can also improve grip. The bottom surfaces of the toe pad 116 and the heel pad 118 need not have the same type and/or size of the groove, pattern, or texture. The toe pad 116 and/or the heel pad 118 can optionally be made from a different material (e.g., more resilient, more flexible, more slip-resistant, or otherwise) than the elongate sole member 110.

Although this disclosure has been described in the context of certain embodiments and examples, it will be understood by those skilled in the art that the disclosure extends beyond the specifically disclosed embodiments to other alternative embodiments and/or uses and obvious modifications and equivalents thereof. In addition, while several variations of the embodiments of the disclosure have been shown and described in detail, other modifications, which are within the scope of this disclosure, will be readily apparent to those of skill in the art. It is also contemplated that various combinations or sub-combinations of the specific features and aspects of the embodiments may be made and still fall within the scope of the disclosure. For example, features described above in connection with one embodiment can be used with a different embodiment described herein and the combination still fall within the scope of the disclosure. It should be understood that various features and aspects of the disclosed embodiments can be combined with, or substituted for, one another in order to form varying modes of the embodiments of the disclosure. Thus, it is intended that the scope of the disclosure herein should not be limited by the particular embodiments described above. Accordingly, unless otherwise stated, or unless clearly incompatible, each embodiment of this invention may comprise, additional to its essential features described herein, one or more features as described herein from each other embodiment of the invention disclosed herein.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a sub combination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, 0.1 degree, or otherwise. Additionally, as used herein, "gradually" has its ordinary meaning (e.g., differs from a non-continuous, such as a step-like, change).

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A prosthetic foot comprising:
an elongate sole member having a toe end defining a toe end of the prosthetic foot and a heel end defining a heel end of the prosthetic foot;
a first upper member having a proximal end and a distal end and including a curve between the proximal and distal ends of the first upper member, the proximal end coupled to an adapter and the distal end coupled to the elongate sole member at an attachment location rearward of the toe end of the elongate sole member; and
a second upper member having a proximal end and a distal end and including a curve between the proximal and distal ends of the second upper member, the proximal end of the second upper member coupled to the adapter and the distal end of the second upper member terminating near the attachment location, wherein the second upper member is pre-compressed such that the distal end of the second upper member is biased toward the first upper member or the elongate sole member.

2. The prosthetic foot of claim 1, wherein the first or second upper member is generally C-shaped.

3. The prosthetic foot of claim 1, further comprising a first spacer between the distal ends of the first and second upper members.

4. The prosthetic foot of claim 3, wherein the distal end of the second upper member is configured to slide along the first spacer during ambulation.

5. The prosthetic foot of claim 3, wherein the first spacer results in a gap between the first and second upper members along a portion of lengths of the first and second upper members, the gap being maintained throughout ambulation.

6. The prosthetic foot of claim 5, wherein the gap is further maintained by an adapter spacer between the proximal ends of the first and second upper members.

7. The prosthetic foot of claim 1, further comprising a second spacer between the distal end of the first upper member and the elongate sole member at or near the attachment location.

8. The prosthetic foot of claim 1, further comprising a heel bumper between the first upper member and the elongate sole member, the heel bumper located rearward of the attachment location.

9. The prosthetic foot of claim 8, further comprising a foam sheet extending from near the distal end of the first upper member along at least a partial length of the first upper member, the foam sheet being between the first upper member and the heel bumper.

10. The prosthetic foot of claim 8, wherein the heel bumper is generally wedge shaped, a thickness of the heel bumper being smaller at an anterior end than at a posterior end.

11. The prosthetic foot of claim 10, wherein the heel bumper comprises three stepped sections on a side facing the first upper member, wherein a posterior end of a first stepped section is shorter than a posterior end of a second stepped section, and the posterior end of the second stepped section is shorter than a posterior end of a third stepped section.

12. The prosthetic foot of claim 11, wherein the first stepped section is closer to the anterior end of the heel bumper and pre-compressed to minimize air gap between the heel bumper and the first upper member.

13. The prosthetic foot of claim 11, wherein lengths of the first, second, and third stepped sections are determined based on a position of the adapter, and wherein the position of the adapter defines a theoretical load line at ⅓ of a length of the prosthetic foot from the heel end.

14. A prosthetic foot comprising:
- a first foot member having a proximal end and a distal end;
- a second foot member having a proximal end and a distal end, the proximal ends of the first and second foot members being coupled to an adapter, the adapter comprising an adapter spacer between the proximal ends of the first and second foot members; and
- a spacer between the distal ends of the first and second foot members, wherein the spacer and the adapter spacer result in a gap between the first and second foot members along a portion of the length of the first and second foot members, the gap being maintained throughout ambulation, and wherein the distal end of the second foot member is configured to slide over the spacer relative to the distal end of the first foot member.

15. The prosthetic foot of claim 14, wherein the second foot member is pre-compressed such that the distal end of the second foot member is biased toward the first foot member.

16. The prosthetic foot of claim 14, further comprising an elongate sole member having a toe end defining a toe end of the prosthetic foot and a heel end defining a heel end of the prosthetic foot, wherein the distal end of the first foot member is coupled to the elongate sole member at an attachment location rearward of the toe end of the elongate sole member.

17. The prosthetic foot of claim 16, wherein the distal end of the second foot member terminates near the attachment location and wherein, during push off, the distal end of the second foot member slides toward the toe end along the spacer to reduce a lever arm length of the second foot member.

18. The prosthetic foot of claim 16, further comprising a second spacer between the distal end of the first foot member and the elongate sole member at or near the attachment location.

19. The prosthetic foot of claim 16, further comprising a heel bumper between the first foot member and the elongate sole member, the heel bumper located rearward of the attachment location.

20. The prosthetic foot of claim 19, further comprising a foam sheet extending from near the distal end of the first foot member along at least a partial length of the first foot member, the foam sheet being between the first foot member and the heel bumper.

* * * * *